(12) United States Patent
Liu et al.

(10) Patent No.: US 10,251,605 B2
(45) Date of Patent: Apr. 9, 2019

(54) BANDAGE TYPE OF CONTINUOUS GLUCOSE MONITORING SYSTEM

(71) Applicant: Verily Life Sciences LLC, Mountain View, CA (US)

(72) Inventors: Zenghe Liu, Alameda, CA (US); Brian Otis, Saratoga, CA (US); Jaclyn Leverett Wasson, Berkeley, CA (US); William James Biederman, Berkeley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 209 days.

(21) Appl. No.: 14/623,012

(22) Filed: Feb. 16, 2015

(65) Prior Publication Data
US 2016/0235365 A1 Aug. 18, 2016

(51) Int. Cl.
*A61B 5/00* (2006.01)
*A61B 5/145* (2006.01)
(Continued)

(52) U.S. Cl.
CPC .......... *A61B 5/6833* (2013.01); *A61B 5/0004* (2013.01); *A61B 5/07* (2013.01);
(Continued)

(58) Field of Classification Search
CPC ... A61B 5/0002; A61B 5/0059; A61B 5/1455; A61B 5/14551; A61B 5/14552;
(Continued)

(56) References Cited

U.S. PATENT DOCUMENTS

| 4,677,528 A | * | 6/1987 | Miniet ................ H01L 23/5387 235/488 |
| 5,165,407 A | | 11/1992 | Wilson et al. |

(Continued)

FOREIGN PATENT DOCUMENTS

| JP | H03-024452 A | 2/1991 |
| JP | 2007-203092 A | 8/2007 |

(Continued)

OTHER PUBLICATIONS

International Search Report and Written Opinion for International Application No. PCT/US2016/017512 dated May 6, 2016.

(Continued)

*Primary Examiner* — Eric Winakur
*Assistant Examiner* — Chu Chuan (JJ) Liu
(74) *Attorney, Agent, or Firm* — McDonnell Boehnen Hulbert & Berghoff LLP

(57) ABSTRACT

A flexible, body-mountable analyte sensing device includes a flexible substrate configured for mounting to skin of a living body. The sensing device additionally includes a sensor probe attached to the flexible substrate and configured to penetrate the skin such that a sensor disposed on the sensor probe can detect an analyte in interstitial fluid. The sensor probe can include an elongate extension of the flexible substrate. The sensor can be, for example, an electrochemical sensor or an optical sensor. The sensing device is configured to wirelessly indicate detected concentrations or other information about the analyte in the interstitial fluid. The flexible substrate of the sensing device is configured to be adhered or otherwise mounted to the skin in a manner that minimally impacts activities of the living body.

20 Claims, 8 Drawing Sheets

(51) Int. Cl.
*A61B 5/1473* (2006.01)
*A61B 5/1459* (2006.01)
*A61B 5/07* (2006.01)

(52) U.S. Cl.
CPC .......... *A61B 5/1451* (2013.01); *A61B 5/1459* (2013.01); *A61B 5/1473* (2013.01); *A61B 5/14503* (2013.01); *A61B 5/14532* (2013.01); *A61B 5/6846* (2013.01); *A61B 5/6848* (2013.01); *A61B 5/0002* (2013.01); *A61B 5/14546* (2013.01); *A61B 5/14735* (2013.01); *A61B 2560/0412* (2013.01); *A61B 2560/063* (2013.01)

(58) Field of Classification Search
CPC . A61B 5/14532; A61B 5/1459; A61B 5/1451; A61B 5/1473; A61B 5/1486; A61B 5/0004; A61B 5/0205; A61B 5/14503; A61B 5/14546; A61B 5/6833; A61B 5/6846; A61B 5/6848
See application file for complete search history.

(56) References Cited

U.S. PATENT DOCUMENTS

| | | | |
|---|---|---|---|
| 5,957,854 A * | 9/1999 | Besson | A61B 5/14552 600/509 |
| 6,175,752 B1 * | 1/2001 | Say | A61B 5/14532 600/365 |
| 7,652,188 B2 | 1/2010 | Levanon et al. | |
| 7,949,382 B2 | 5/2011 | Jina | |
| 8,202,697 B2 | 6/2012 | Holmes | |
| 8,326,652 B2 | 12/2012 | Sweeney | |
| 8,385,998 B2 | 2/2013 | Zhang et al. | |
| 8,512,245 B2 | 8/2013 | Markle et al. | |
| 8,609,426 B2 | 12/2013 | Silver | |
| 8,764,657 B2 | 7/2014 | Curry et al. | |
| 8,792,954 B2 | 7/2014 | Brister et al. | |
| 8,849,379 B2 | 9/2014 | Abreu | |
| 8,956,289 B2 | 2/2015 | Kitajima et al. | |
| 8,972,196 B2 | 3/2015 | Peyser et al. | |
| 8,979,755 B2 | 3/2015 | Szydlo-Moore et al. | |
| 9,007,781 B2 | 4/2015 | Moenin et al. | |
| 9,072,476 B2 | 7/2015 | Shah et al. | |
| 9,248,232 B2 | 2/2016 | Yodfat et al. | |
| 2005/0113658 A1 | 5/2005 | Jacobson et al. | |
| 2005/0148887 A1 * | 7/2005 | Reiter | A61B 5/0002 600/508 |
| 2007/0073129 A1 | 3/2007 | Shah et al. | |
| 2007/0100219 A1 * | 5/2007 | Sweitzer | A61B 5/14551 600/323 |
| 2007/0100222 A1 | 5/2007 | Mastrototaro et al. | |
| 2007/0173711 A1 | 7/2007 | Shah et al. | |
| 2008/0009692 A1 | 1/2008 | Stafford | |
| 2008/0079565 A1 | 4/2008 | Koyama | |
| 2008/0114227 A1 | 5/2008 | Haar et al. | |
| 2009/0240121 A1 | 9/2009 | Bickoff | |
| 2010/0094112 A1 | 4/2010 | Heller et al. | |
| 2010/0198034 A1 | 8/2010 | Thomas et al. | |
| 2010/0200538 A1 | 8/2010 | Petisce et al. | |
| 2010/0268046 A1 | 10/2010 | Say et al. | |
| 2010/0270180 A1 | 10/2010 | Liu et al. | |
| 2011/0077490 A1 | 3/2011 | Simpson et al. | |
| 2011/0319734 A1 | 12/2011 | Gottlieb et al. | |
| 2012/0018302 A1 | 1/2012 | Shiraki et al. | |
| 2012/0190989 A1 | 7/2012 | Kaiser et al. | |
| 2012/0277667 A1 | 11/2012 | Yodat et al. | |
| 2012/0296187 A1 | 11/2012 | Henning et al. | |
| 2013/0041235 A1 | 2/2013 | Rogers et al. | |
| 2013/0060105 A1 * | 3/2013 | Shah | A61B 5/14532 600/316 |
| 2013/0076531 A1 | 3/2013 | San Vicente et al. | |
| 2013/0131478 A1 | 5/2013 | Simpson et al. | |
| 2013/0197332 A1 | 8/2013 | Lucisano et al. | |
| 2013/0274563 A1 | 10/2013 | Duesterhoft et al. | |
| 2014/0180137 A1 | 6/2014 | Stivoric et al. | |
| 2014/0275899 A1 * | 9/2014 | Gottlieb | A61B 5/14532 600/347 |
| 2015/0005589 A1 | 1/2015 | Bly et al. | |
| 2015/0018639 A1 | 1/2015 | Stafford | |
| 2015/0119662 A1 | 4/2015 | Larson et al. | |

FOREIGN PATENT DOCUMENTS

| | | |
|---|---|---|
| JP | 2007-205989 A | 8/2007 |
| JP | 2008-109847 A | 5/2008 |
| JP | 2009-508639 T | 3/2009 |
| JP | 2012-026910 A | 2/2012 |
| JP | 2012-517597 T | 8/2012 |
| JP | 2012-531948 T | 12/2012 |
| JP | 2013-009710 A | 1/2013 |
| JP | 2013-534439 T | 9/2013 |
| JP | 2014-523793 T | 9/2014 |
| JP | 2014-529481 T | 11/2014 |
| WO | 2013028784 A1 | 2/2013 |
| WO | 2013172929 A1 | 11/2013 |
| WO | 2014145484 A2 | 9/2014 |
| WO | 2014159229 A1 | 10/2014 |
| WO | 2015017712 | 2/2015 |
| WO | 2015017712 A1 | 2/2015 |

OTHER PUBLICATIONS

Getting starting with Guardian REAL-Time Continuous Glucose Monitoring, product guide, 2009, Medtronic, Northridge, CA.
Dexcom G4 Platinum Professional Continuous Glucose Monitoring System, User's guide, 2014, Dexcom, IncG.
International Search Report and Written Opinion of International Application No. PCT/US2016/017946 dated Jun. 1, 2016.
Getting starting with Guardian REAL-Time Continuous Glucose Monitoring, Product manual, 2009, Medtronic, Northridge, CA.
Guardian REAL-Time Continuous Glucose Monitoring System, User guide, 2006, Medtronic MiniMed, Northridge, CA.
Dexcom G4 Platinum Professional Continuous Glucose Monitoring System, User's guide, 2014, Dexcom, Inc.
Dexcom G4 Platinum Continuous Glucose Monitoring System, Quick start guide, 2013, Dexcom, Inc. San Diego, CA.
Jonah Comstock, "Medtronic showcases smartphone-enabled continuous glucose monitoring," MobiHealthNews, http://mobihealthnews.com, Sep. 24, 2014.
Pickup, J.C., et al., "Fluorescence-based glucose sensors," Biosensors and Bioelectronics, p. 2555-2565, 20 (2005).
Klonoff, D.C., "Overview of Fluorescence Glucose Sensing: A Technology with a Bright Future," Journal of Diabetes Science and Technology, p. 1242-1250, vol. 6, Issue 6, (2012).

* cited by examiner

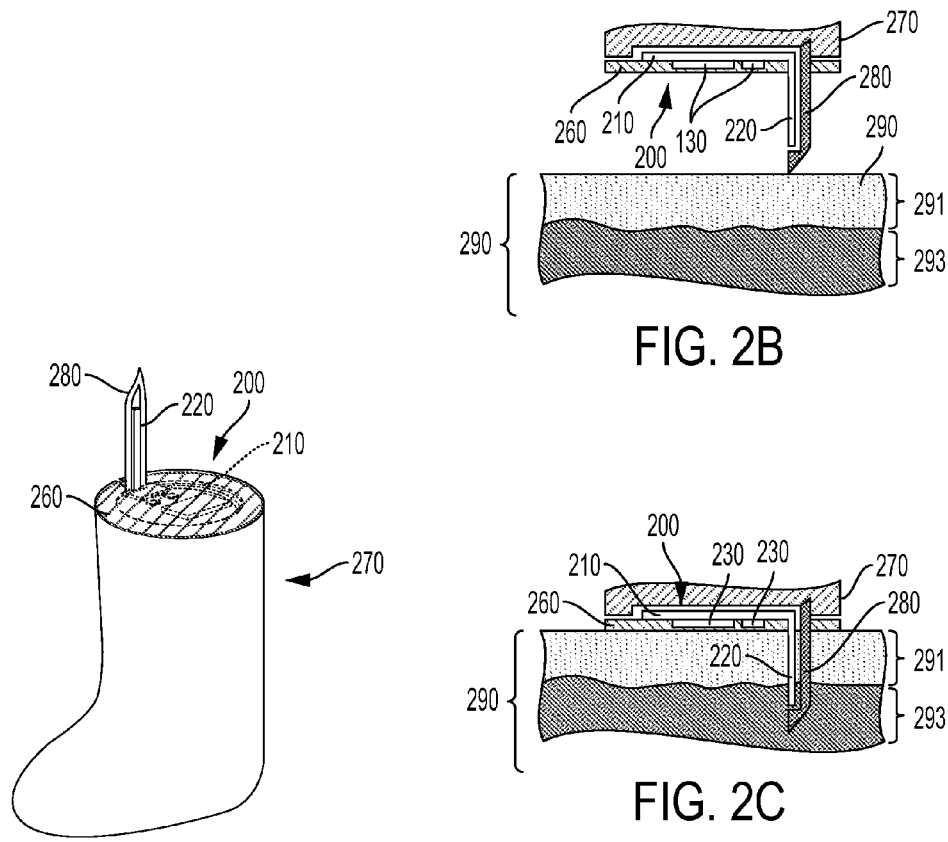
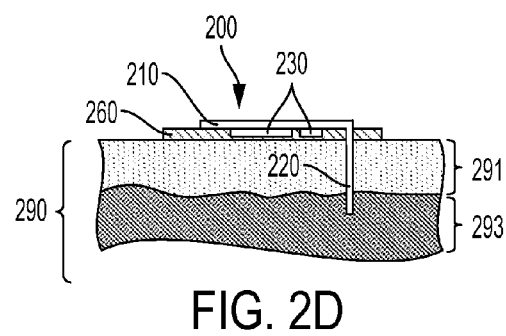

BANDAGE TYPE OF CONTINUOUS GLUCOSE MONITORING SYSTEM

BACKGROUND

Unless otherwise indicated herein, the materials described in this section are not prior art to the claims in this application and are not admitted to be prior art by inclusion in this section.

Certain medical conditions or states can be characterized by slow changes of a physiological property (e.g., a blood glucose concentration) over long periods of time and/or by infrequent, short-timescale events. Such physiological properties can be measured periodically (e.g., by periodically accessing blood of a person). Additionally or alternatively, an implanted or wearable device could be employed to provide continuous or near-continuous measurement of such physiological properties. Such implantable or wearable devices can be battery powered and/or powered by radio frequency energy or other wireless energy sources. Further, such devices can be configured to indicate measured physiological properties wirelessly (e.g., by using an RFID antenna and transmitter, by using a Bluetooth antenna and transmitter).

SUMMARY

Some embodiments of the present disclosure provide a body-mountable device including: (i) a flexible substrate, wherein the flexible substrate is configured to be mounted to a skin surface; (ii) a sensor probe, wherein a first end of the sensor probe is attached to the flexible substrate, and wherein a second end of the sensor probe is configured to extend beneath the skin surface to contact interstitial fluid; (iii) a sensor, wherein the sensor is disposed at the second end of the sensor probe, and wherein the sensor is configured to detect an analyte in the interstitial fluid; and (iv) one or more electronic components disposed on the flexible substrate, wherein the one or more electronic components are configured to (a) use the sensor to obtain data related to the analyte and (b) communicate the data related to the analyte to an external device.

Some embodiments of the present disclosure provide a body-mountable device including: (i) a flexible substrate, wherein the flexible substrate is configured to be mounted to a skin surface; (ii) probe means, wherein a first end of the probe means are attached to the flexible substrate, and wherein a second end of the probe means are configured to extend beneath the skin surface to contact interstitial fluid; (iii) sensor means, wherein the sensor means are disposed at the second end of the probe means, and wherein the sensor means are configured to detect an analyte in the interstitial fluid; and (iv) one or more electronic components disposed on the flexible substrate, wherein the one or more electronic components are configured to (a) use the sensor means to obtain data related to the analyte and (b) communicate the data related to the analyte to an external device.

Some embodiments of the present disclosure provide a method including: (i) mounting a body-mountable device to a skin surface, wherein the body-mountable device includes: (a) a flexible substrate; (b) a sensor probe, wherein a first end of the sensor probe is attached to the flexible substrate, and wherein the sensor probe is configured to extend beneath the skin surface to contact interstitial fluid; (c) a sensor, wherein the sensor is disposed at a second end of the sensor probe, and wherein the sensor is configured to detect an analyte in the interstitial fluid; and (d) one or more electronic components disposed on the flexible substrate; (ii) operating the body-mountable device to obtain, by the one more electronic components, data related to the analyte using the sensor; and (iii) operating the body-mountable device to communicate, by the one or more electronic components, the data related to the analyte to an external device.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A is an aspect view of an example body-mountable device removably mounted to an example insertion device.

FIG. 2B is a cross-sectional view of the body-mountable device and insertion device of FIG. 2A, positioned proximate to skin of a living body.

FIG. 2C is a cross-sectional view of the body-mountable device, insertion device, and skin of a living body of FIG. 2B, showing the body-mountable device and insertion device penetrating the skin.

FIG. 2D is a cross-sectional view of the body-mountable device, insertion device, and skin of a living body of FIG. 2B, showing the body-mountable device penetrating the skin and the insertion device retracted from the skin.

DETAILED DESCRIPTION

Figure 1A:
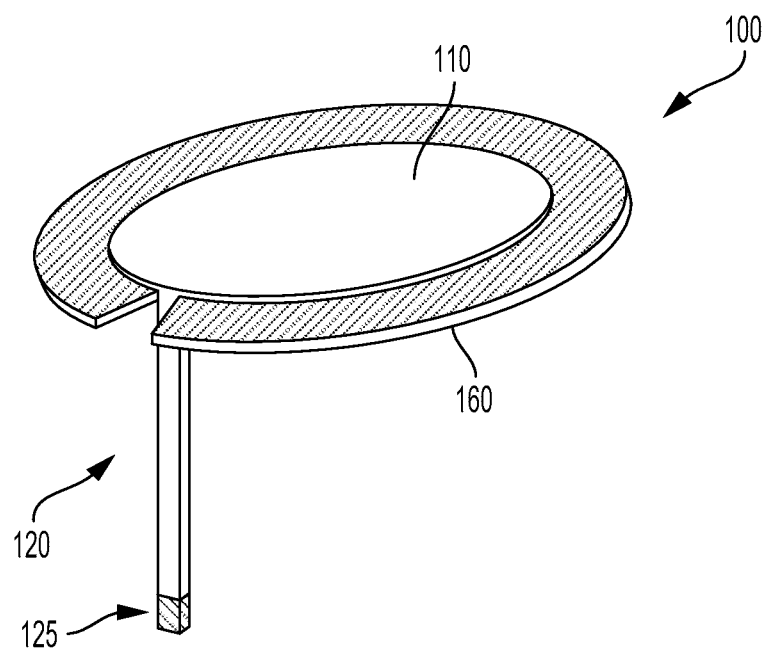
FIG. 1A is a top aspect view of an example body-mountable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Some embodiments of the present disclosure provide a body-mountable device configured to be mounted to a skin surface (e.g., to skin of the upper arm or abdomen of a person), with one or more sensors for quantitatively and qualitatively testing an analyte concentration in interstitial fluid (e.g., interstitial fluid within or beneath the skin) in situ and in real-time. The one or more sensors are mounted on a sensor probe that is configured to penetrate the skin and that is attached to a flexible substrate of the device. Further, the flexible substrate is configured to be mounted to the skin surface (e.g., by use of glue, tape, dry adhesive, or other adhesive means). The flexibility of the flexible substrate could provide a sensing platform that minimally interferes with activities of a person to whom the sensing platform is mounted and/or that can be mounted to a person comfortably for protracted periods of time. Those of skill in the art will recognize that the sensing platform described herein may be provided in devices that could be mounted on a variety of portions of the human body to measure concentrations of an analyte in other fluids than interstitial fluid (e.g., to measure an analyte in a tear fluid, blood, saliva, or some other fluid or tissue of the body). Those of skill in the art will also recognize that the sensing platform described herein may be provided in devices that could be mounted in locations other than locations on a human body to measure concentrations of an analyte in a fluid proximate to the mounting location of the devices.

The sensor probe can be configured to penetrate to a specified depth within the skin (e.g., to a depth within the dermis, to a subcutaneous depth) such that at least one sensor disposed on the sensor probe can measure an analyte in fluid (e.g., interstitial fluid) at the specified depth. The sensor probe could be flexible or rigid; in some examples, the sensor probe could comprise an elongate extension of the flexible substrate material. The sensor probe could be configured to pierce the skin (e.g., could be sufficiently rigid and/or sharpened such that the sensor probe can be driven into the skin). Additionally or alternatively, the sensor probe could be configured to pierce and/or penetrate the skin in combination with an insertion device. For example, the sensor probe could be configured to be mounted within the channel of a half-needle or to some other means for piercing the skin; the half needle or other piercing means could be used to pierce the skin and to subsequently retract, leaving the sensor probe in place penetrating the skin. One or more sensors could be disposed at the end of such a sensor probe and/or at one or more additional locations along the length of such a sensor probe.

A sensing platform can include a power source, electronics, and an antenna all disposed on the flexible substrate configured to be mounted to a skin surface. The electronics can operate one or more sensors (e.g., a sensor disposed at the distal end of a sensor probe) to perform measurements of an analyte (e.g., to measure the concentration of the analyte in interstitial fluid within or beneath the skin). The electronics could additionally operate the antenna to wirelessly communicate the measurements from the sensor or other information to an external reader or some other remote system via the antenna. One or more of the power source, antenna, electronics, or other components of the sensing platform could be flexible; for example, the power source could include a thin, flexible lithium ion battery.

Some embodiments of the present disclosure further include a user interface configured to receive inputs from a user (e.g., a user to whose body the device is mounted) and/or present outputs to the user to provide some application(s) of the body-mountable device. Such user-interface elements (e.g., displays, sensors, buttons) could be flexible and/or mounted to the flexible substrate of the sensing platform. In some examples, the user interface could provide means for changing or setting an operational state of the sensing device and/or for causing the performance of some function by the sensing platform. For example, the user interface could provide means for a user to cause the sensing platform to perform a measurement of the physiological property using the sensor, to set the sensing platform into a sleep or other low-power state, to set a rate of operation of the sensor to detect the physiological property, or to control some other aspect of operation or function of the sensing platform. In some examples, the user interface could provide means for inputting calibration or other data to the sensing platform, e.g., for inputting calibration data related to the operation of the sensor to detect the physiological property. Additionally or alternatively, the user interface could provide means for inputting information about the state of a user of the sensing platform, e.g., to indicate a physical or mental state of the user, to indicate an activity of the user, to indicate that the user has eaten a meal or taken a drug, or to indicate some other information. The user interface could provide means for indicating information to a user, for example, information about the operation of the sensing platform (e.g., battery charge state, an amount of free memory), detected physiological properties (e.g., a blood glucose level detected using the sensor), or some other information available to the sensing platform.

In some examples, the sensor disposed at the end of the sensor probe of the sensing platform can include two or more electrodes configured to detect or measure an analyte electrochemically. The two or more electrodes could include a working electrode selectively sensitive to the analyte and a reference electrode. In some examples, exposing the sensor to a target fluid causes a potentiometric voltage to develop between the working electrode and the reference electrode that can indicate the concentration of the analyte near the working electrode. Additionally or alternatively, a specified voltage could be applied between the reference electrode and the working electrode and an amount of current that responsively flows through the working electrode could be related to the concentration of the analyte near the working electrode and/or the rate at which the analyte diffuses to the working electrode. The working electrode can be made selectively sensitive to the analyte by localizing a substance (e.g., a reagent, a protein, an enzyme) that selectively interacts with the analyte on or near the working electrode of the sensor. Such an analyte-selective substance can be localized within an analyte-permeable polymer layer that is disposed on the working electrode. Additionally or alternatively, such an analyte-selective substance can be localized on the surface of the working electrode by crosslinking.

In some examples, the sensor disposed at the end of the sensor probe of the sensing platform can include an analyte-sensitive substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of a substance disposed at the end of the sensor probe could be related to the presence, concentration, or some other property of the analyte. The sensor platform could include a light emitter and/or a light detector configured to illuminate and to receive light emitted from the analyte-sensitive substance, respectively, in order to determine the optical property of the substance that is related to the analyte. In some examples, the sensor probe could include an optical fiber and the analyte-selective substance could be disposed on a distal end of such an optical fiber. In such examples, a light emitter and/or a light detector could be disposed at a proximal end of the optical fiber, such that the light emitter and light detector illuminate and received light from the analyte-sensitive substance via the optical fiber. In such examples, the light emitter and/or light detector could be disposed on the flexible substrate of the sensor platform (e.g., as part of the electronics disposed on the flexible substrate).

In some examples, an analyte-sensitive substance (e.g., a substance that specifically engages in a chemical reaction with the analyte, a substance that specifically binds to the analyte, or a substance that has a property that is related to the presence or concentration of the analyte) could be disposed on a surface of the sensing platform (e.g., on a metal surface of an electrode, on a surface of an optical fiber) and/or within a polymer, gel, or other layer that is permeable to the analyte and that is disposed on such a surface. Additionally or alternatively, a polymer, gel, or other layer that is permeable to the analyte could be disposed over the working electrode and/or other elements of the sensor probe to protect the elements of the sensor probe or according to some other application. In some examples, a permeability, thickness, or other properties of such an analyte-permeable layer could be specified to control a rate of diffusion of the analyte from interstitial fluid to a sensor (e.g., to a metal electrode surface of the sensor) or to some other element of the sensing platform (e.g., to an analyte-selective reagent disposed proximate to an electrode, optical fiber, or some other element of the sensing platform). In some examples, a protective or other polymer layer could be a hydrogel, e.g., a hydrogel that includes units of 2-hydroxethyl methacrylate.

The sensing platform can be powered via one or more batteries in the sensing platform and/or by energy from an external source. In some examples, the one or more batteries could be flexible and disposed on the flexible substrate to allow for flexibility of the overall sensing platform and/or of elements of the sensing platform that are able to be mounted to skin (e.g., to provide greater comfort and/or to minimize effect on user activities when mounted to skin of a user). Such flexible batteries could include flexible lithium ion batteries. Batteries of a sensing platform as described herein could be single-use or could be rechargeable. Rechargeable batteries could be recharged by power provided by radio frequency energy harvested from an antenna disposed on the flexible substrate. The antenna can be arranged as a loop of conductive material with leads connected to the electronics. In some embodiments, such a loop antenna can also wirelessly communicate the information (e.g., measurements of the analyte made using a sensor of the sensing platform) to an external reader (e.g., to a cellphone) by modifying the impedance of the loop antenna so as to modify backscatter radiation from the antenna. Additionally or alternatively, the sensing platform could include a chip, dipole, or other type of antenna for transmitting and/or reflecting RF energy to indicate information to an external reader. Further, such antennas could be used to transfer additional information, e.g., to indicate a temperature, light level, or other information detected by the sensing platform, to receive commands or programming from an external device, or to provide some other functionality.

II. Example Flexible Biosensor Platform

Figure 1B:
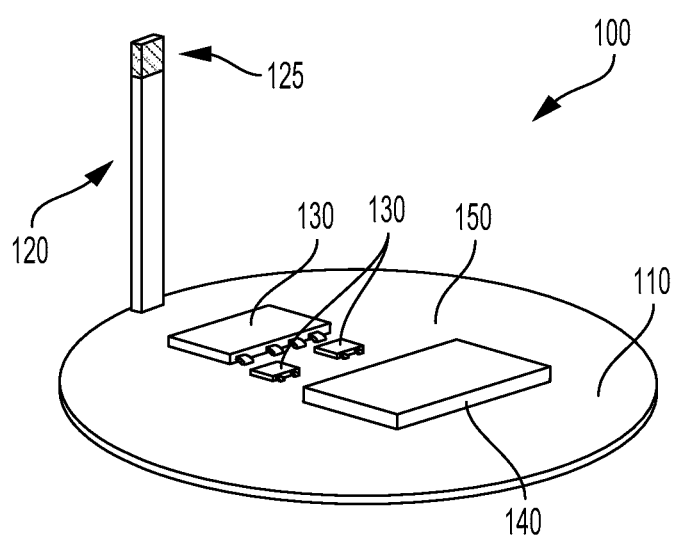
FIG. 1B is a bottom aspect view of the example body-mountable device shown in FIG. 1A.

FIG. 1A is a top view of an example body-mountable sensing platform 100. FIG. 1B is a bottom view of the example body-mountable sensing platform shown in FIG. 1A. It is noted that relative dimensions in FIGS. 1A and 1B are not necessarily to scale, but have been rendered for purposes of explanation only in describing the arrangement of the example body-mountable sensing platform 100. The body-mountable device 100 is formed of a flexible substrate 110 shaped (as an illustrative example) as a circular disk. A sensor probe 120 extends from the flexible substrate 110 and is configured to penetrate a skin surface (e.g., to penetrate into skin of the upper arm or abdomen of a human body). A sensor 125 is disposed at a distal end of the sensor probe 120. The sensor 125 is configured to detect an analyte (e.g., glucose) in interstitial or other fluids under and/or within the skin when the sensor probe 120 penetrates the skin. An adhesive layer 160 is provided to mount the flexible substrate 110 to a skin surface (the adhesive layer 160 is not shown in FIG. 1B, to allow illustration of elements of the body-mountable sensing platform 100 that are disposed on the bottom surface 150 of the flexible substrate 110). The body-mountable sensing platform 100 additionally includes electronics 130 disposed on the flexible substrate 110 and configured to provide various applications of the sensing platform 100 including, e.g., operating the sensor 125 to detect the analyte, recording information about the analyte in a memory of the electronics 130, and communicating information about the analyte (e.g., by using an antenna to wirelessly indicate such information) to an external system. The antenna (not shown) could be configured as a loop antenna on bottom surface 150 (e.g., encircling electronics 130), or the antenna could be configured as a chip antenna or some other configuration. A battery 140 is provided to power the body-mountable sensing platform 100 (e.g., to power the electronics 130). Components (e.g., antennas, batteries, electronics, user interface elements) could additionally or alternatively be disposed on the top surface of the flexible substrate 110 (i.e., the surface of the flexible substrate 110 opposite the bottom surface 150).

The flexible substrate 110 is configured to be mounted to a skin surface. In the example shown in FIGS. 1A and 1B, this includes a layer of adhesive 160 being provided to adhere the flexible substrate 110 to a skin surface. Additional or alternative means could be provided to mount the flexible substrate 110 to a skin surface. For example, a liquid or gel adhesive could be applied to the skin surface and/or to the flexible substrate 110 to mount the flexible substrate 110 to the skin surface. The flexible substrate 110 could be placed on the skin surface and secured using tape or other adhesives. In some examples, the body-mountable sensing platform 100 could include a dry adhesive configured to removably mount the flexible substrate 110 to a skin surface. Other means for mounting the flexible substrate 110 or other elements of the body-mountable sensing platform 100 to a skin surface or to other elements or aspects of a living body are anticipated. Further, in some embodiments, a body-mountable sensing platform 100 could be provided that is configured to be emplaced proximate a target fluid (e.g., interstitial fluid, synovial fluid, blood, tears, saliva, mucus) without mounting to a skin surface or other tissue surface. For example, a body-mountable sensing platform 100 as described herein could be configured to be placed between the teeth and cheek of a living body, on the eye of a living body, or at some other location of a living body without being mounted to a particular tissue surface.

The flexible substrate 110 can have a thickness, shape, composition, and/or other properties specified such that the flexible substrate 110 can be mounted to a skin surface of a living body and further such that such mounting minimally interferes with activities of the living body (e.g., motions of the living body). This could include the flexible substrate 110 being sufficiently flexible that mounting of the flexible substrate 110 to the skin surface causes a minimum of discomfort. The flexible substrate 110 could be composed of polyimide or some other flexible polymeric or other material. The flexible substrate could have a thickness less than approximately 100 microns. Further, the flexible substrate 110 could have a size specified to minimally interfere with activities of the living body. For example, the flexible substrate 110 could have size (e.g., a diameter of a circular portion, as illustrated in FIGS. 1A and 1B) less than approximately 11 millimeters. Diameter and thickness values are provided for explanatory purposes only. Further, the shape of the flexible substrate 110 could be different from that illustrated in FIGS. 1A and 1B or elsewhere herein; for example, the flexible substrate 110 could have an elongate shape, a square or rectangular shape, or some other shape according to an application. For example, the flexible substrate 110 could have an elongate shape to provide sufficient area for disposition of electronics, batteries, antennas, or other components on the flexible substrate 110 while minimally impeding motion and/or deformation of the skin surface to which the flexible substrate 110 is mounted (e.g., by being formed and/or mounted to the skin surface such the orientation of the elongate shape of the flexible substrate 110 is perpendicular to a direction of strain of the skin surface).

One or more surfaces of the flexible substrate 110 (e.g., the bottom surface 150) could be used as a platform for mounting electronics such as chips (e.g., via flip-chip mounting) and for patterning conductive materials (e.g., via deposition techniques) to form electrodes, antenna(e), and/or connections. The composition of the flexible substrate 110 could be chosen to allow for the formation and/or disposition of such elements of the body-mountable sensing platform 100. For example, the flexible substrate 110 could be composed of polyimide or some other polymeric and/or metallic material(s) such that metal contacts, traces, and interconnects can be patterned directly on the surface of the flexible substrate 110 (e.g., by sputtering, CVD, or some other deposition process) and/or on a coating or layer formed on one or more surfaces of the flexible substrate 110. Further, such patterned structures and/or other elements disposed on the flexible substrate 110 (e.g., electronics 130, battery 140, antennas) could, in combination with the flexible substrate 110, have a thickness or other property specified to provide the overall body-mountable sensing platform 100 with flexibility. For example, the flexible substrate 110 in combination with electronics 130 and battery 140 disposed thereon could have a thickness less than approximately 0.5 millimeters.

The electronics 130 disposed on the flexible substrate 110 could include a variety of devices. For example, the electronics 130 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 110. Further, antennas, electrodes, capacitors, resistors, or other components could be formed from such traces or other interconnects formed on the surface of the flexible substrate 110. The electronics 130 can include logic elements configured to operate the sensor 125 to detect an analyte, an antenna (e.g., a loop, dipole, or other type of antenna formed on the flexible substrate 110, a chip antenna disposed on the flexible substrate 110) to wirelessly indicate information (e.g., concentration levels) about the detected analyte, and/or to provide other functions. A loop, dipole, or other type of antenna can be one or more layers of conductive material patterned on a surface (e.g., 150) of the flexible substrate 110 to form one or more specified conductive shapes (e.g., a ring, a spiral, a curved or straight line, an elliptical or rectangular patch, a fractal). Electrical interconnects (e.g., traces), antennas, and/or conductive electrodes (e.g., for an electrochemical analyte sensor, etc.) can be formed from conductive materials patterned on the flexible substrate 110 by a process for precisely patterning such materials, such as deposition, lithography, etc. The conductive materials patterned on the flexible substrate 110 can be, for example, gold, platinum, palladium, titanium, carbon, aluminum, copper, silver, silver-chloride, conductors formed from noble materials, metals, combinations of these, etc.

The sensor probe 120 is an elongate element of the body-mountable sensing platform 100 that is configured to penetrate a skin surface such that the sensor 125 located at the distal end of the sensor probe 120 is in contact with a fluid (e.g., interstitial fluid, blood) containing an analyte of interest (e.g., glucose) when the sensor probe 120 is penetrating the skin. For example, the sensor probe 120 could be more than approximately 2 millimeters long. The sensor probe 120 could have a length or other properties specified such that, when the sensor probe 120 penetrates skin and/or the flexible substrate 120 is mounted to a skin surface, a sensor (e.g., 125) or other element(s) disposed on the sensor probe 120 contact tissue at a specified depth within the skin (e.g., tissue of the dermis of the skin, subcutaneous tissue). For example, the sensor probe 120 could have a length between approximately 500 microns and approximately 6000 microns. Further, the sensor probe 120 could have one or more dimensions specified to provide sufficient area for electrodes or other elements disposed on the sensor probe 120, to minimally interfere with the skin (e.g., by requiring a minimal incision or other alteration of the skin to provide for penetration of the sensor probe 120), or according to some other application. For example, the sensor probe 120 could have a width between approximately 25 microns and approximately 400 microns.

The sensor probe 120 could be composed of a variety of materials and elements formed by a variety of processes. The sensor probe 120 could be composed of a flexible material (e.g., polyimide) or a relatively inflexible material; further, a thickness, width, shape, or other properties of the sensor probe 120 could be specified to provide a degree of flexibility or inflexibility. For example, a flexible sensor probe 120 could have a width between approximately 25 microns and approximately 400 microns and/or a thickness less than approximately 100 microns. In some examples, the sensor probe 120 could be formed from the same material as the flexible substrate 110; i.e., the sensor probe 120 could be an elongate portion of the flexible substrate 110 that extends from a portion of the flexible substrate 110 that is configured to be mounted to a skin surface and/or on which electronics 130 or other components are disposed. Alternatively, the sensor probe 120 could be attached to the flexible substrate 110. For example, the sensor probe 120 could include optical fiber(s), flexible element(s) (e.g., an elongate piece of polyimide or other polymeric or metallic substance), wire(s), elongate pieces of shaped silicon, or other elements adhered, welded, bonded, or otherwise attached to the flexible substrate 110. Alternatively, such sensor probes could be used for other applications and/or in combination with components or devices other than a flexible substrate (e.g., 110) as described herein.

The sensor probe 120 could be configured to pierce skin to allow the sensor probe 120 to penetrate the skin and dispose the sensor 125 in contact with interstitial or other fluids within the skin. For example, the sensor probe 120 could be sharpened, could include one or more rigid materials to facilitate application of force to the sensor probe 120 to pierce the skin (e.g., stainless steel tubes, rods, sheets, and/or needles), or could be otherwise configured to pierce skin. In some examples, the sensor probe 120 could include materials having a stiffness or some other property that changes to allow the sensor probe 120 to be used to pierce the skin during a first period of time and subsequently to become less rigid or to change some other property according to an application. In some examples, the sensor probe 120 could include a material configured to initially have a high rigidity, to allow for piercing of skin, and to soften when the sensor probe penetrates the skin for a period of time. For example, the sensor probe 120 could include a piece of poly-2-hydroxyethyl methacrylate (poly-HEMA) or some other hydrogel configured to soften by absorbing water (e.g., from interstitial fluid) once the sensor probe 120 has penetrated the skin. In another example, the sensor probe 120 could include a stiff material that is configured to dissolve into and/or be absorbed by the skin (e.g., polylactic acid (PLA)). Additionally or alternatively, the sensor probe 120 could be inserted into skin by another device that is configured to pierce the skin, or into an incision into the skin formed by another device. For example, the sensor probe 120 could be configured to be mounted within the channel of a half-needle of a device (e.g., a device configured to insert the sensor probe 120 into skin and/or to mount the flexible substrate 110 to a skin surface) such that the half-needle could pierce the skin and subsequently be retracted, leaving the sensor probe 120 in place penetrating the skin.

Note that the depiction of a body-mountable sensor platform 100 having a single sensor probe 120 on a distal end of which a single sensor 125 is disposed is intended as a non-limiting, illustrative example. A particular sensor probe of a body-mountable sensing platform could include additional sensors disposed at different locations on the particular sensor probe. For example, a particular sensor probe could include a plurality of sensors disposed along the length of the particular sensor probe to allow for detection of some property of skin (e.g., a concentration of an analyte within the skin) at a variety of depths within the skin. A body-mountable sensor platform could include more than one sensor probe and such more than one sensor probes could have respective widths, lengths, thicknesses, sensors, sensor locations, or other properties. Further, a body-mountable sensing platform could include sensors that are not disposed at a distal end or other locations on a sensor probe. For example, one or more sensors could be disposed on a flexible substrate (e.g., 110) or other element(s) of such a body-mountable sensing platform.

While not illustrated in FIG. 1A or 1B, a body-mountable sensing platform (e.g., 100) as described herein could include one or more user interface elements configured to receive user input (e.g., from a user whole skin the sensor probe 120 is penetrating and whose skin surface the flexible substrate 110 is mounted to) and/or to indicate information. A body-mountable sensing platform could include lights (e.g., discrete LEDs), displays (e.g., flexible OLED displays), vibration motors, electrohaptic stimulators, or other means for indicating information to a user. Such indicated information could include information about a detected analyte (e.g., a detected concentration of the analyte), information about the status of the body-mountable sensing platform (e.g., battery charge status, free memory space status), alerts (e.g., alerts that a concentration of the analyte is within/outside of a specified range, alerts that a particular health state has been detected, alerts that a user should perform some medical task and/or seek medical attention), or some other information. A body-mountable sensing platform could include buttons, capacitive touch-sensing elements configured to detect touches and/or gestures, temperature sensors configured to detect touches, or other means for detecting input from a user. Such input could include instructions to perform some task (e.g., to operate the sensor 125 to detect the analyte), to change an operational state (e.g., to start and/or stop regular detection of the analyte, to change a frequency at which the analyte is detected), to indicate a personal and/or health state of a user (e.g., to indicate that the user is experiencing nausea, lightheadedness, etc.), to indicate that an event has occurred (e.g., that the user has administered/been administered a drug), or some other input/instructions to the body-mountable sensing platform.

A variety of sensor probes configured to penetrate skin, and devices (e.g., body-mountable sensing platforms) including such sensor probes, are described herein. Such sensor probes could be configured and/or operated to penetrate skin through a pre-existing cut, puncture, incision, or other entry through the surface of the skin into tissue (e.g., dermal tissue, subcutaneous tissue) containing an analyte-containing fluid of interest (e.g., interstitial fluid). Such a pre-existing entry could be formed for the purpose of inserting the sensor probe by a lancet, needle, or other instrument configured to pierce the skin. Additionally or alternatively, the sensor probe and/or some other element of a body-mountable sensing platform could be configured to pierce the skin, e.g., by including rigid elements, by including a sharpened end, or by being configured in some other way to allow piercing of the skin. In some examples, the sensor probe (and body-mountable sensing platform, in embodiments wherein the sensor probe is an element of such a sensing platform) could be removably mounted to an insertion device configured to pierce the skin in combination with the sensor probe and to retract leaving the sensor probe in place (i.e., penetrating the skin).

FIG. 2A illustrates an example body-mountable sensing platform 200 removably mounted to an example insertion device 270. The body-mountable sensing platform 200 includes a flexible substrate 210, a sensor probe 220 attached to the flexible substrate 210, and an adhesive layer 260 configured to adhere the flexible substrate 210 to a skin surface. The sensor probe 220 is configured to penetrate the skin and includes a sensor (not shown) configured to detect an analyte (e.g., to measure a concentration of glucose) in a fluid within the skin (e.g., in interstitial fluid) when the sensor probe 220 penetrates the skin. The sensor probe 220 is coupled to a needle 280 of the insertion device 270. The needle 280 is a half-needle; that is, the needle 280 includes a channel along the length of the needle 280 in which the sensor probe 220 is disposed. The needle 280 is configured to pierce skin such that the needle 280 and the coupled sensor probe 220 penetrate the skin. That is, the needle is sufficiently rigid and/or has an end that is sufficiently sharp that force can be applied to the insertion device 270 such that the needle 280 pierces the skin. The insertion device 270 can then be moved away from the skin, retracting the needle 280 while the sensor probe 220 remains inserted in (i.e., penetrating) the skin and the flexible substrate 210 remains mounted on the skin surface.

FIGS. 2B-2D show, in cross-section, the process of using the insertion device 270 to pierce skin 290. The skin 290 includes an epidermal layer 291 and a dermal layer 293. FIG. 2B shows the body-mountable sensing platform 200 removably mounted to the insertion device 270 such that the sensor probe 220 of the sensing platform 200 is coupled to the needle 280 of the insertion device (that is, in this example, that the sensor probe 220 is disposed within a channel of the needle 280). As shown in FIG. 2B, the insertion device 270 and sensing platform 200 removably mounted thereto are disposed proximate the skin 290, but have not yet pierced and/or penetrated the skin 290.

FIG. 2C shows the insertion device 270 and sensing platform 200 after the needle 280 (and sensor probe 220 coupled thereto) has been inserted into the skin 290 (i.e., the needle 280 has pierced the skin). Further, the flexible substrate 210 has been mounted, via the adhesive action of the adhesive layer 260, to the skin 290 surface. The sensor probe 220 penetrates the skin 290 such that the distal end of the sensor probe 220 is located in the dermal layer 293 of the skin 290 (e.g., such that a sensor disposed on the end of the sensor probe 220 could detect an analyte in interstitial or other fluids present in the dermal layer 293). FIG. 2D shows the sensing platform 200 after the needle 280 of the insertion device 270 has been retracted. The sensor probe 220 continues to penetrate the skin 290 such that the distal end of the sensor probe 220 is located in the dermal layer 293 of the skin 290.

Note that the illustrated insertion device 270 and sensing platform 200 and use thereof to pierce and/or penetrate the skin 290, are intended as non-limiting illustrative examples of such devices and methods. An insertion device 270 and/or sensing platform 200 could have different shapes, include different components and/or elements, be configured different, and/or differ in some other way as will be clear to one of skill in the art. For example, the insertion device could consist of a disk to which a half-needle or other penetrating means are attached and to which a body-mountable sensing platform could be removably mounted. In some examples, the insertion device 270 could be configured to provide some additional functionality, e.g., could be configured to receive communications from the sensing platform (e.g., to received information related to the detected analyte), to recharge a sensing platform, to activate a sensing platform, or to provide some other functionality. In some examples, an insertion device could include a driving mechanism (e.g., a spring-loaded mechanism, a servomechanism including one or more solenoids, motors, or other electromechanical actuators) configured to drive a needle (and sensor probe coupled thereto) into skin (e.g., to a specified depth within the skin, at a sufficiently high speed to minimize user discomfort). In some examples, the needle 280 could be retractable into the insertion device 270 for safety.

Note that the mounting of body-mountable sensing platforms to skin surfaces of living bodies, and the penetration of such skin by sensor probes of sensing platforms, are intended as non-limiting illustrative examples of devices and methods described herein. Such devices and systems could be used to detect analytes in other fluids in other tissues by penetrating such other tissues with sensor probes and/or mounting flexible substrates to surfaces of such tissues. For example, sensor probes, flexible substrates, and/or sensing platforms as described herein could be used to detect an analyte within a mucosal epithelium (e.g., within the mucosa of a mouth, nose, or other mucosa of a living body). Additionally or alternatively, sensor probes, flexible substrates, and/or sensing platforms as described herein could be used to detect analytes in a variety of fluids without penetrating tissues (e.g., to detect an analyte in a tissue present in a volume of a living body, e.g., to detect an analyte in peritoneal fluid by disposing a sensing-platform as described herein within the peritoneal cavity of a living body). Further, systems and devices as described herein could be used to detect analytes in fluids of an animal and/or plant body, and/or to detect an analyte in a natural environment (e.g., a stream, a lake) and/or an artificial environment (e.g., fluids of a pharmaceutical process, fluids of a water treatment process, fluids of a food processing process).

A sensor disposed at a distal end of a sensor probe or at some other location of a body-mountable sensing platform as described herein could include a variety of components and/or substances configured in a variety of ways. In some examples, such sensors could include one or more substances that selectively interact with an analyte. For example, such substances could include proteins, enzymes, aptamers, DNA, RNA, nano-structures, antibodies, reagents, nano-structured surfaces, or other substances configured to selectively bind to, catalyze a reaction of, or otherwise selectively interact with an analyte of interest. Such an analyte-sensitive substance could be disposed on a surface of a sensing platform (e.g., on a metal surface of an electrode, on a surface of an optical fiber, on some other surface of a sensor probe and/or flexible substrate) and/or within a polymer, gel, or other layer that is permeable to the analyte and that is disposed on such a surface.

In some examples, an analyte-selective substance could be disposed on a surface of a sensing platform (e.g., on an electrode surface) by crosslinking the substance on the surface (e.g., using glutaraldehyde to crosslink the analyte-sensitive substance). In some examples, an analyte-selective substance can be disposed within a polymer layer formed on a surface of a sensing platform. Such a polymer layer can be permeable to the analyte and contain a reagent that selectively reacts with the analyte to create a reaction product that can be sensed directly by an electrode and/or by some other element (e.g., a fluorophore or other substance that selectively interacts with the reaction product). In some examples, the polymer layer that contains the analyte-selective substance is a hydrogel that includes 2-hydroxyethyl methacrylate units. Such a hydrogel could contain additional polymer units or other chemicals to adjust a permeability of the hydrogel to the analyte, to bind the analyte-selective substance within the hydrogel, in increase a degree of crosslinking of the hydrogel, or to specify one or more other properties of the hydrogel. For example, such a hydrogel could additionally include di(ethylene glycol) dimethacrylate units.

In some examples, the sensor of a sensing platform can include two or more electrodes configured to detect or measure the analyte electrochemically. The two or more electrodes could include a working electrode selectively sensitive to the analyte and a reference electrode. In some examples, exposing the sensor to a target fluid (e.g., interstitial fluid) causes a potentiometric voltage to develop between the working electrode and the reference electrode that can indicate the concentration of the analyte near the working electrode. Additionally or alternatively, a specified voltage could be applied between the reference electrode and the working electrode and an amount of current that responsively flows through the working electrode could be related to the concentration of the analyte near the working electrode and/or the rate at which the analyte diffuses to the working electrode (e.g., through a hydrogel layer containing an analyte-selective substance and/or through a hydrogel layer disposed to protect the working electrode and/or other components of the sensor).

In some examples, the sensor of a sensing platform can include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of a substance disposed at the end of the sensor probe could be related to the presence, concentration, or some other property of the analyte. The sensor platform could include a light emitter and/or a light detector configured to illuminate and to receive light emitted from the analyte-sensitive substance, respectively, in order to determine the optical property of the substance that is related to the analyte. In some examples, a sensor probe of the sensing platform could include an optical fiber and the analyte-selective substance could be disposed on a distal end of such an optical fiber. In such examples, a light emitter and/or a light detector could be disposed at a proximal end of the optical fiber, such that the light emitter and light detector illuminate and received light from the analyte-sensitive substance via the optical fiber. In such examples, the light emitter and/or light detector could be disposed on a flexible substrate of the sensor platform (e.g., as part of electronics disposed on the flexible substrate).

In some examples, a polymer, gel, or other layer that is permeable to the analyte could be disposed over to one or more components of the sensor (e.g., over a working electrode, over a layer containing and/or composed of an analyte-selective substance) and/or other elements of a sensing platform to protect the elements of the sensing platform or according to some other application. In some examples, a permeability, thickness, or other properties of such an analyte-permeable layer (and/or of a similar layer containing an analyte-selective substance) could be specified to control a rate of diffusion of the analyte from interstitial fluid to a sensor (e.g., to a metal electrode surface of the sensor) or to some other element of the sensing platform (e.g., to an analyte-selective substance disposed proximate to an electrode, optical fiber, or some other element of the sensing platform). In some examples, a protective or other polymer layer could be a hydrogel, e.g., a hydrogel that includes units of 2-hydroxyethyl methacrylate and/or units of di(ethylene glycol) dimethacrylate.

III. Example Electronics of a Flexible Biosensor Platform

Figure 3:
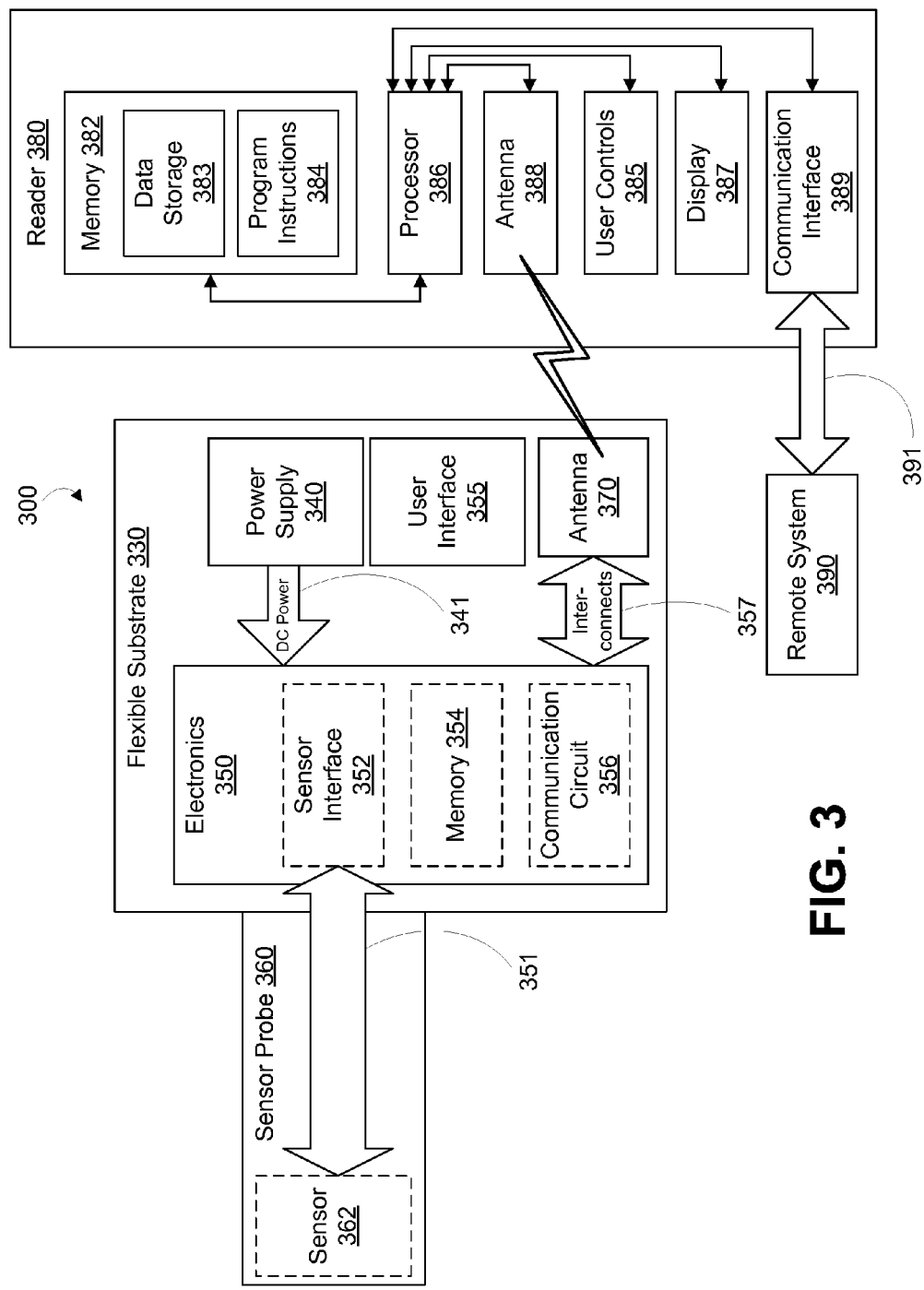
FIG. 3 is a block diagram of an example system that includes a body-mountable device in wireless communication with an external reader.

FIG. 3 is a block diagram of a system that includes a body-mountable sensor platform 300 in wireless communication with an external reader 380. The body-mountable sensor platform 300 includes a flexible substrate 330 that is made of a flexible polymeric or metallic material formed to be mounted to a skin surface. The flexible substrate 330 provides a mounting surface for a power supply 340, electronics 350, user interface 355, and a communication antenna 370. The power supply 340 supplies operating voltages to the electronics 350 and/or other elements of the sensing platform 300. The antenna 370 is operated by the electronics 350 to communicate information to and/or from the body-mountable sensing platform 300. The antenna 370, the electronics 350, user interface 355, and the power supply 340 can all be situated on the flexible substrate 330.

The flexible substrate 330 can have a thickness, shape, composition, and/or other properties specified such that the flexible substrate 330 can be mounted to a skin surface of a living body and further such that such mounting minimally interferes with activities of the living body (e.g., motions of the living body). This could include the flexible substrate 330 being sufficiently flexible that mounting of the flexible substrate 330 to the skin surface causes a minimum of discomfort. The flexible substrate 330 could be composed of polyimide or some other flexible polymeric or other material. One or more surfaces of the flexible substrate 330 could be used as a platform for mounting components or elements of the antenna 370, the electronics 350, user interface 355, and the power supply 340 such as chips (e.g., via flip-chip mounting) and conductive materials (e.g., via deposition techniques) that form electrodes, antenna(e), and/or connections. The composition of the flexible substrate 330 could be specified such that metal contacts, traces, and interconnects can be patterned directly on the surface of the flexible substrate 330 (e.g., by sputtering, CVD, or some other deposition process) and/or on a coating or layer formed on one or more surfaces of the flexible substrate 330.

The electronics 350 disposed on the flexible substrate 330 could include a variety of devices. For example, the electronics 350 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 330. Further, antennas, electrodes, capacitors, resistors, or other components could be formed from such traces or other interconnects formed on the surface of the flexible substrate 330. The electronics 350 can include logic elements configured to operate the sensor 362 to detect an analyte, an antenna (e.g., a loop, dipole, or other type of antenna formed on the flexible substrate 330, or a chip antenna disposed on the flexible substrate 330) to wirelessly indicate information (e.g., concentration levels) about the detected analyte, and/or to provide other functions. Electrical interconnects (e.g., traces), antennas, and/or conductive electrodes (e.g., for an electrochemical analyte sensor, etc.) can be formed from conductive materials patterned on the flexible substrate 330 by a process for precisely patterning such materials, such as deposition, lithography, etc. The conductive materials patterned on the flexible substrate 330 can be, for example, gold, platinum, palladium, titanium, carbon, aluminum, copper, silver, silver-chloride, conductors formed from noble materials, metals, combinations of these, etc.

The body-mountable sensing platform 300 further includes a sensor probe 360 that is attached to the flexible substrate 330. The sensor probe 360 is an elongate element of the body-mountable sensing platform 300 that is configured to penetrate a skin surface such that a sensor 362 located at a distal end of the sensor probe 360 is in contact with a fluid (e.g., interstitial fluid or blood) containing an analyte of interest (e.g., glucose) when the sensor probe 360 is penetrating the skin. That is, the sensor probe 360 is configured to extend beneath the skin surface into an epidermal, dermal, or subcutaneous tissue of a body that includes the skin surface. The sensor probe 360 could be composed of a flexible material (e.g., polyimide) or a relatively inflexible material; further, a thickness, width, shape, or other properties of the sensor probe 360 could be specified to provide a degree of flexibility or inflexibility. In some examples, the sensor probe 360 could be formed from the same material as the flexible substrate 330; i.e., the sensor probe 360 could be an elongate portion of the flexible substrate 330 that extends from a portion of the flexible substrate 330 that is configured to be mounted to a skin surface and/or on which electronics 350 or other components are disposed. Alternatively, the sensor probe 360 could be attached to the flexible substrate 330. For example, the sensor probe 360 could include optical fiber(s), wire(s), elongate pieces of shaped silicon, patterned conductive traces, or other elements adhered, welded, bonded, or otherwise attached to the flexible substrate 330. Alternatively, such sensor probes could be used for other applications and/or in combination with components or devices other than a flexible substrate (e.g., 330) as described herein.

The substrate 330 includes one or more surfaces suitable for mounting the electronics 350 (including a sensor interface 352, a memory 354, and a communication circuit 356), the power supply 340, and the antenna 370. The flexible substrate 330 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. For example, the antenna 370 can be formed by depositing a pattern of gold or another conductive material on the flexible substrate 330. Similarly, interconnects 341, 351, 357 between the electronics 350 and the power supply 340, between the sensor interface 352 and the sensor 362, and between the communication circuit 356 and the antenna 370, respectively, can be formed by depositing suitable patterns of conductive materials on the substrate 330. A combination of microfabrication techniques including, without limitation, the use of photoresists, masks, deposition techniques and/or plating techniques can be employed to pattern materials on the substrate 330. The substrate 330 can be a material, such as polyimide, polyethylene terephthalate ("PET"), parylene, or another material sufficient to structurally support the circuitry and/or electronics.

The power supply 340 is configured to provide energy to power the electronics 350. For example, the power supply 340 could include a battery. Such a battery could be flexible, e.g., the battery could be a flexible lithium-ion battery or some other type of flexible battery. The battery could be flexible to allow the flexible substrate 330 to which the battery is mounted to flex in response to deformation and/or motion of a skin surface to which the flexible substrate 330 is mounted. Such flexibility could be provided to increase the comfort of a living body to which the sensing platform 300 is mounted and/or to minimally interfere with motions and/or activities of such a living body. A battery (or combination of batteries provided as part of the power supply 340) could have a capacity sufficient to power the device for a protracted period of time, e.g., 18 hours, a week, or some other protracted period of time of periodic operation of the sensor 362, antenna 370, and memory 354 to detect an analyte, to record information related to the analyte in the memory 354, and to wirelessly communicate such detected information to the external reader 380. For example, the battery could be a flexible battery with a capacity of more than approximately 60 microamp-hours and a thickness of less than approximately 0.5 millimeters.

In some examples, the power supply 340 could include a rechargeable battery and could further include some means for recharging such a battery. For example, the power supply 340 could include contacts disposed on a surface of the flexible substrate 330 and configured to receive electrical power from complimentary contacts of a charging device (e.g., the external reader 380). In another example, the sensing platform 300 could include a loop antenna (e.g., a loop antenna comprising conductive traces patterned on the flexible substrate 330) and the power supply 340 could be configured to use the loop antenna to receive RF energy from an external device (e.g., the external reader 380); in some examples, such an RF-energy-receiving antenna could be the same antenna as the antenna 370 used to communicate with external devices.

The user interface 355 is configured to receive inputs from a user (e.g., a user to whose body the device is mounted) and/or present outputs to the user to provide some application(s) of the sensing platform 300. Such user-interface elements (e.g., displays, sensors, buttons) could be flexible and/or mounted to the flexible substrate 330 of the sensing platform 300. In some examples, the user interface 355 could provide means for changing or setting an operational state of the sensing platform 300 and/or for causing the performance of some function by the sensing platform 300. For example, the user interface 355 could provide means for a user to cause the sensing platform 300 to perform a measurement of the physiological property using the sensor 362, to set the sensing platform 300 into a sleep or other low-power state, to set a rate of operation of the sensor 362 to detect the physiological property, or to control some other aspect of operation or function of the sensing platform 300. In some examples, the user interface 355 could provide means for inputting calibration or other data to the sensing platform 300, e.g., for inputting calibration data related to the operation of the sensor 362 to detect the physiological property. Additionally or alternatively, the user interface 355 could provide means for inputting information about the state of a user of the sensing platform 300, e.g., to indicate a physical or mental state of the user, to indicate an activity of the user, to indicate that the user has eaten a meal or taken a drug, or to indicate some other information. The user interface 355 could provide means for indicating information to a user, for example, information about the operation of the sensing platform 355 (e.g., battery charge state, an amount of free memory), detected physiological properties (e.g., a blood glucose level detected using the sensor 362), or some other information available to the sensing platform 300.

The user interface 355 could be configured to detect a variety of inputs. The user interface 355 could be configured to detect sound (e.g., voice commands), motions of the sensing platform 300 (e.g., a gesture that includes motion of the skin surface to which the sensing platform is mounts), contact between the sensing platform 300 and a finger or other portion of a user's body, or some other inputs. For example, the user interface 355 could be configured to detect a location, motion, pressure, gesture, or other information about objects (e.g., a finger or other body part) near the sensing platform 300. The user interface 355 could include a capacitive touch sensor configured to detect a single touch, multiple touches, gestures, swipes, or other inputs. The user interface 355 could include flexible components. In some examples, the user interface 355 could include one or more elements in common with the sensor 362. For example, the sensor 362 of the sensing platform 300 could be configured to detect a temperature of the skin surface to which the sensing platform 300 is mounted; additionally, the sensor 362 could be used to detect inputs (e.g., contact between the sensing platform 300 and a finger or other object) by detecting changes over time in the temperature detected using the sensor 362.

The user interface 355 could be configured to provide a variety of different types of information via a variety of means. The user interface 355 could indicate information related to the operational state of the sensing platform 300 (e.g., to indicate a battery charge state or free memory space of the device) and/or related to the physiological property detected using the sensor 362 (e.g., to indicate a blood glucose level detected using the sensor 362). The out user interface 355 could be used to indicate a course of action that a user could take (e.g., to administer a drug, to seek medical assistance). The user interface 355 could be used to indicate some alert generated by the sensing platform 300 (e.g., an alert that a measured physiological property is outside of specified limits, and alert that a user is experiencing an adverse health state). The user interface 355 could include light-emitting elements (e.g., LEDs, OLEDs, displays), color-changing elements (e.g., e-ink elements or displays, LCDs), haptic elements (e.g., vibrators, buzzers, electrohaptic elements), acoustical elements (e.g., buzzers, speakers), or some other elements configured to indicate some information, e.g., to a user. The user interface 355 could include flexible elements, e.g., the user interface 355 could include a flexible OLED display.

The sensor interface module 352 and connection 351 between the sensor interface module 352 and sensor 362 could take a variety of forms according to the methods used to detect an analyte in fluid (e.g., interstitial fluid) to which the sensor 362 is exposed. The sensor 362 can include an analyte-selective substance that selectively interacts with the analyte in the fluid. The analyte-selective substance can include proteins, enzymes, reagents, ionophores, antibodies, fluorophores, nano-structured surfaces and/or structures, or other substances that selectively bind to, react with, change one or more properties in response to the presence of, or otherwise selectively interact with the analyte. The sensor 362 and sensor interface 352 can then detect the selective interaction between the analyte and the analyte-selective substance to detect a presence, concentration, or other properties of the analyte.

Such detection can include detecting the interaction between the analyte and the analyte-selective substance directly (e.g., by detecting a change in an optical property of the analyte-selective substance in response to interaction with the analyte, by detecting a change in electrical potentials at the sensor 362 due to accumulation of a charged analyte by the analyte-selective substance) or indirectly (e.g., by detecting a reaction product of the selective reaction of the analyte, e.g., by detecting hydrogen peroxide produced by oxidation of the analyte by the analyte-selective substance). Direct or indirect detection of the analyte could include electrochemical detection (i.e., the sensor could include two or more electrodes configured to electrochemically detect the analyte), optical detection (i.e., the sensor 362 and/or the sensor interface 352 could include a light emitter and/or light detector configured to detect an optical property of the analyte and/or the analyte-selective substance that is related to the presence, concentration, or some other property of the analyte), or some other detection means.

In some examples, the sensor 362 includes at least a reference electrode and a working electrode. The working electrode is selectively sensitive to an analyte of interest, for example, by having an analyte-selective substance localized proximate to the working electrode (e.g., by being disposed on a surface of the working electrode, by being disposed in an analyte-permeable polymer layer disposed on the working electrode). The sensor interface 352 is configured to operate the sensor 362 to electrochemically detect the analyte.

In some examples, the electrochemical analyte sensor 362 can be a potentiometric sensor. In such examples, a voltage can develop between the working and reference electrodes related to a concentration of analyte in a fluid to which the working electrode is exposed. Thus, the sensor interface 352 can measure a magnitude of the potentiometric voltage between the working electrode and the reference electrode to provide an indication of analyte concentration. In such embodiments, the sensor interface 352 can include a high-impedance voltmeter configured to measure the voltage difference between working and reference electrodes while substantially preventing the flow of current through the working and reference electrodes.

Additionally or alternatively, the electrochemical analyte sensor 362 can be an amperometric sensor. In such examples, the sensor interface 352 can apply a specified voltage between the reference electrode and the working electrode. The applied voltage can drive an electrochemical current through the working electrode that is related to the concentration of an analyte near the working electrode. Such an electrochemical current can be related to redox or other reactions of the analyte at the surface of the working electrode and/or could be related to redox or other reactions of reaction products of the analyte at the surface of the working electrode (e.g., reaction products produced by reaction of the analyte due to selective interaction with the analyte-selective substance). Thus, the sensor interface 352 can measure a magnitude of the amperometric current passing through the working electrode to provide an indication of analyte concentration. In such embodiments, the sensor interface 352 can include a specified voltage source (to provide the specified voltage between the reference electrode and the working electrode) and a current meter configured to measure the current passing through the working electrode due to the applied specified voltage. In some examples, the sensor 362 could additionally include a counter electrode through which a return current (i.e. a current having a magnitude substantially equal but opposite to the current passing through the working electrode) could pass, such that substantially no current passes through the reference electrode. Such an embodiment could allow for the reference electrode to provide a more stable voltage relative to the fluid to which the sensor 362 is exposed.

In some examples, the sensor 362 could include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. In some examples, such an analyte-selective substance could include a protein or other element configured to selectively bind to the analyte and to experience a conformation change in response to such binding. A fluorophore and a quencher could be attached to the protein such that the distance between the fluorophore and the quencher is related to whether the protein is bound to the analyte; as a result, the degree of fluorescence of the fluorophore could be related to whether the protein is bound to the analyte. Additionally or alternatively, a color, saturation, absorption spectrum, or some other optical property of a substance disposed at the end of the sensor probe could be related to the presence, concentration, or some other property of the analyte.

In such examples, the sensor interface 352 and/or the sensor 362 could include a light emitter and/or a light detector configured to illuminate and/or to receive light emitted from the analyte-sensitive substance, respectively, in order to determine the optical property of the substance that is related to the analyte. In some examples, the light emitter and/or light detector could be disposed as part of the sensor 362 (i.e., disposed on the sensor probe 360) and connected to the sensor interface 352 via conductive interconnects (e.g., the sensor interconnect 351 could include traces patterned or otherwise disposed on the sensor probe 360). Additionally or alternatively, the sensor probe 360 could include an optical fiber and the analyte-selective substance could be disposed on a distal end of such an optical fiber. In such examples, the light emitter and/or a light detector could be disposed at a proximal end of the optical fiber (e.g., on the flexible substrate 330 as part of the sensor interface 352), such that the light emitter and light detector illuminate and/or receive light from the analyte-sensitive substance via the optical fiber.

The memory 354 could include a variety of volatile and nonvolatile electronic storage elements configured to provide means for the sensing platform 300 to record and/or log detected information about the analyte (e.g., concentrations measured using the sensor 362 at a plurality of points in time) and/or other information detected by or input to (e.g., via user interface components of the sensing platform 300) the sensing platform 300. For example, the memory 354 could include one or more EEPROM memories, flash memories, NVRAM memories, DRAM memories, SRAM memories, flip-flops, or other information storage elements. The memory 354 could have an information storage capacity sufficient to record some specified period of detected information about the analyte at some specified rate of detection; e.g., the memory 354 could have a capacity sufficient to record more than 18 hours, a week, or some other protracted period of time of detected information (e.g., concentrations) about the analyte when detected at a rate of approximately once per minute. Additionally or alternatively, the sensing platform 300 could be in communication with a memory that is external to the sensing platform 300 and that could be used as described above (e.g., to store analyte measurement data, to store and/or access calibration or other configuration data of the sensing platform 300).

While not illustrated in FIG. 3, the body-mountable sensing platform 300 could include one or more user interface elements configured to receive user input (e.g., from a user whole skin the sensor probe 360 is penetrating and whose skin surface the flexible substrate 330 is mounted to) and/or to indicate information. The body-mountable sensing platform 300 could include lights (e.g., discrete LEDs), displays (e.g., flexible OLED displays), vibration motors, electrohaptic stimulators, or other means for indicating information to a user. Such indicated information could include information about a detected analyte (e.g., a detected concentration of the analyte), information about the status of the body-mountable sensing platform (e.g., battery charge status of the power supply 340, free memory status of the memory 354), alerts (e.g., alerts that a concentration of the analyte is within/outside of a specified range, alerts that a particular health state has been detected, alerts that a user should perform some medical task and/or seek medical attention), or some other information. The body-mountable sensing platform 300 could include buttons, capacitive touch-sensing elements configured to detect touches and/or gestures, temperature sensors configured to detect touches, or other means for detecting input from a user. Such input could include instructions to perform some task (e.g., to operate the sensor 362 to detect the analyte), to change an operational state (e.g., to start and/or stop regular detection of the analyte, to change a frequency at which the analyte is detected), to indicate a personal and/or health state of a user (e.g., to indicate that the user is experiencing nausea, light-headedness, etc.), to indicate that an event has occurred (e.g., that the user has administered/been administered a drug), or some other input/instructions to the body-mountable sensing platform 300.

The electronics 350 include a communication circuit 356 for sending and/or receiving information via the antenna 370. The communication circuit 356 can optionally include one or more oscillators, mixers, frequency injectors, etc. to modulate and/or demodulate information on a carrier frequency to be transmitted and/or received by the antenna 370. In some examples, the body-mountable sensing platform 300 is configured to indicate information (e.g., detected analyte concentrations using the sensor 362) by modulating an impedance of the antenna 370 in a manner that is perceivably by the external reader 380. For example, the communication circuit 356 can cause variations in the amplitude, phase, and/or frequency of backscatter radiation from the antenna 370, and such variations can be detected by the reader 380. Such wireless communication could be compatible with one or more existing backscatter wireless communications standards, e.g., RFID. Additionally or alternatively, the communication circuit 356 and antenna 370 could be configured to transmit wireless signals according to some other method, e.g., according to the Bluetooth (e.g., Bluetooth Low Energy), ZigBee, WiFi, LTE, and/or some other wireless communications standard or scheme. In some examples, such communications (e.g., data transmitted from the sensor platform 300, operational instructions transmitted to the sensor platform 300) could be cryptographically secured; that is, the wireless communications link could be encrypted.

The sensor interface 352 is connected to the sensor 362 via a sensor interconnect 351. In some examples, the sensor interconnect 351 could include a patterned conductive material (e.g., gold, platinum, palladium, titanium, copper, aluminum, silver, metals, combinations of these, etc.) to connect electrodes, light emitters, light detectors, or other components of the sensor 362 to a terminal on a or other component(s) comprising the sensor interface 352. Similarly, the electronics 350 are connected to the antenna 370 via interconnects 357. Additionally or alternatively, the sensor interconnect 351 could include an optical fiber or other means for transmitting light between the sensor 362 and the sensor interface 352. For example, the sensor interface 352 could comprise a light emitter and/or light detector and the sensor 362 could include an analyte-sensitive substance that has an optical property that is related to the presence, concentration, or some other property of the analyte. In such examples, the light emitter and/or a light detector could be disposed at a proximal end of the optical fiber, such that the light emitter and light detector illuminate and receive light from the analyte-sensitive substance via the optical fiber of the sensor interconnect 351. Other configuration of the sensor interconnect 351 are anticipated (e.g., capillary tubes, microfluidic elements, etc.).

It is noted that the block diagram shown in FIG. 3 is described in connection with functional modules for convenience in description. However, embodiments of the body-mountable sensing platform 300 can be arranged with one or more of the functional modules ("sub-systems") implemented in a single chip, integrated circuit, and/or physical feature or on multiple such elements.

The external reader 380 includes an antenna 388 (or group of more than one antenna) to send and receive wireless signals 371 to and from the body-mountable sensing platform 300. The external reader 380 also includes a computing system with a processor 386 in communication with a memory 382. The external reader 380 can also include one or more of user controls 385, a display 387, and a communication interface 389. The memory 382 is a non-transitory computer-readable medium that can include, without limitation, magnetic disks, optical disks, organic memory, and/or any other volatile (e.g. RAM) or non-volatile (e.g. ROM) storage system readable by the processor 386. The memory 382 can include a data storage 383 to store indications of data, such as sensor readings (e.g., acquired using the sensor 362), program settings (e.g., to adjust behavior of the body-mountable sensing platform 300 and/or external reader 380), etc. The memory 382 can also include program instructions 384 for execution by the processor 386 to cause the external reader 380 to perform processes specified by the instructions 384. For example, the program instructions 384 can cause external reader 380 to perform any of the function described herein. For example, program instructions 384 may cause the external reader 380 to provide a user interface that allows for retrieving information communicated from the body-mountable sensing platform 300 (e.g., sensor outputs from the sensor 362) by displaying that information on the display 387 in response to commands input through the user controls 385. The external reader 380 can also include one or more hardware components for operating the antenna 388 to send and receive the wireless signals 371 to and from the body-mountable sensing platform 300. For example, oscillators, frequency injectors, encoders, decoders, amplifiers, filters, etc. can drive the antenna 388 according to instructions from the processor 386.

The external reader 380 can also be configured to include a communication interface 389 to communicate signals via a communication medium 391 to and from a remote system 390. For example, the remote system 390 may be a smart phone, tablet computer, laptop computer, or personal computer, and communication interface 389 and communication medium 391 may be a Bluetooth module and wireless Bluetooth communication signals, respectively. In this example, the external reader 380 may be configured to send information about the analyte collected using the sensor 362 to the smart phone, tablet computer, laptop computer, or personal computer for storage and offline analysis. In another example, the remote system 390 is a server at a clinic or physician's office, the communication interface 389 is a WiFi radio module, and the communication medium 391 is elements of the internet sufficient to enable the transfer of data between the remote server and the WiFi radio module. A physician may use this data to make determinations or diagnoses related to the subject's condition. Further, the external reader 380 may be configured to receive signals from a remote server, such as instructions sent by a physician at a remote location to, for example, increase or decrease sampling frequency. Communication interface 389 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 380 can be a smart phone, digital assistant, or other portable computing device with wireless connectivity sufficient to provide the wireless communication link 371. The external reader 380 can also be implemented as an antenna module that can be plugged in to a portable computing device, such as in an example where the communication link 371 operates at carrier frequencies not commonly employed in portable computing devices. In some instances, the external reader 380 is a special-purpose device configured to be periodically placed relatively near the sensing platform 300 to allow the wireless communication link 371 to operate with a low power budget.

In some examples, the sensor 362 could be configured to detect glucose in the body of a person and the external reader 380 could include or be in contact with an insulin pump. Such an insulin pump could include a supply of insulin and a pump configured to provide the insulin, at a controlled rate, into the body of the person (e.g., through a tube placed in and/or through the skin of the body of the person using, e.g., a needle). In such examples, the insulin pump could be operated based on measurements of glucose levels (e.g., concentrations) in the body of the person detected using the sensor 362. For example, the insulin pump could be operated to provide insulin at a rate based on the detected glucose levels such that the blood glucose levels of the person are maintained within a specified range, or according to some other scheme (e.g., the insulin pump could be operated as part of a feedback loop that includes the sensor 362). Additionally or alternatively, the external reader 380 could include or be in contact with a pump for some other pharmaceutical and could be operated to provide that pharmaceutical at a controlled rate based on a detected level of glucose or of some other analyte detected using the sensor 362.

In an example where the body-mountable sensing platform 300 has been mounted to skin of a living body such that the sensor 362 is in contact with interstitial fluid of the living body, the sensing platform 300 can be operated to detect the analyte (e.g., to measure a concentration of the analyte) in the interstitial fluid. The interstitial fluid is an extravascular fluid that suffuses many of the tissues of a living animal body. The interstitial fluid is continuously replenished by the blood supply through capillaries in the structure of tissue (e.g., dermal tissue, subcutaneous tissue) and includes many biomarkers found in blood that are analyzed to characterize a person's health condition(s). For example, the interstitial fluid includes urea, glucose, calcium, sodium, cholesterol, potassium, phosphate, other biomarkers, etc. The biomarker concentrations in the interstitial can be systematically related to the corresponding concentrations of the biomarkers in the blood, and a relationship between the two concentration levels can be established to map interstitial fluid biomarker concentration values to blood concentration levels. Thus, measuring interstitial fluid analyte concentration levels using sensing platforms as described herein can provide a technique for monitoring analyte levels in comparison to blood sampling techniques performed by lancing a volume of blood to be analyzed outside a person's body. Moreover, the body-mountable sensor platform disclosed here can be operated substantially continuously to enable real time measurement of analyte concentrations or other information about an analyte.

In some embodiments, the body-mountable sensing platform 300 can operate to non-continuously ("intermittently") indicate information related to a detected analyte (e.g., concentration values of the analyte). For example, the body-mountable sensing platform 300 could operate to periodically operate the sensor 362 to detect an analyte and to store information related to the detection of the analyte in the memory 354. The sensing platform 300 could then less frequently operate to transmit stored information relating to more than one detection of the analyte. Additionally or alternatively, a user could operate the external reader 380 to request such information transmission by the sensing platform 300. In another example, the sensing platform 300 could indicate to a user (e.g., via a light, vibration motor, or other user interface element(s) of the sensing platform) that the user should operate the external reader 380 to receive such transmitted information from the sensing platform (e.g., due to the memory 354 being nearly full, due to a battery of the power supply 340 being nearly depleted). Other operations of the systems shown to continuously, periodically, and/or intermittently use the sensor 362 to detect an analyte, use the memory 354 to store information related to the detected analyte, and/or use the antenna 370 to wirelessly indication such information are anticipated.

IV. Example Biosensors

Sensors configured to detect the presence, concentration, or some other property of an analyte of interest could be configured in a variety of ways and incorporated into a variety of different systems of devices. For example, a sensor could be included on a distal end of a sensor probe that is configured to penetrate skin of a living body, such that the sensor can detect the analyte in interstitial (or other fluid) within the skin when the sensor probe penetrates the skin. Further, such sensor probes could be included as part of a body-mountable sensing platform that includes a flexible substrate, to which the sensor probe is attached, and that is configured to be mounted (e.g., by an adhesive layer or some other means) to a skin surface. A sensor could detect the analyte electrochemically (e.g., by detecting a voltage between and/or a current passing through two or more electrodes), optically (by detecting an optical property of the analyte and/or some other element(s) of the environment and/or of the sensor), or by some other means.

A sensor can be configured to detect an analyte by including one or more substances that selectively interact with the analyte. Such substances could have an electrical, optical, or other property that is related to the presence, concentration, or other property of the analyte. Additionally or alternatively, an analyte-selective substance could selectively react with and/or selectively catalyze a reaction of the analyte, and products of such a reaction could be detected by a sensor to allow for detection of the analyte. Analyte-selective substances can coat one or more surfaces of a sensor, can be incorporated into an analyte-permeable layer of polymer, gel, or some other material, or can be localized and/or incorporated on or into a sensor by some other method.

An electrochemical sensor includes at least two electrodes and is configured to electrochemically detect the analyte. This could include operating the two or more electrodes to detect a voltage between two or more of the electrodes, a current passing through one or more of the electrodes, an impedance of one or more of the electrodes, or some other electrochemical variable that can be related to one or more properties of the analyte. Electrodes of such an electrochemical sensor can be composed of one or more metals or metal alloys. Additionally or alternatively, electrodes can include conductive polymers or other conductive materials. The electrodes can be configured to have a specified ohmic resistance, to catalyze certain redox reactions with one or more chemicals (e.g., with the analyte, with a product of a reaction of the analyte that is catalyzed by an analyte-selective substance), to have a specified capacitance to a fluid, to have a stable electrode voltage relative to a fluid, or to have some other specified property.

Figure 4A:
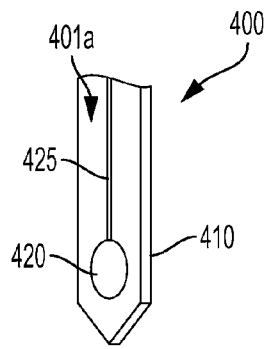
FIG. 4A is a front aspect view of an example electrochemical sensor.
Figure 4B:
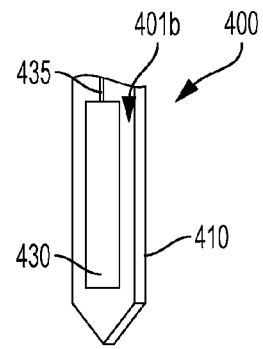
FIG. 4B is a back aspect view of the example electrochemical sensor of FIG. 4A.
Figure 4C:
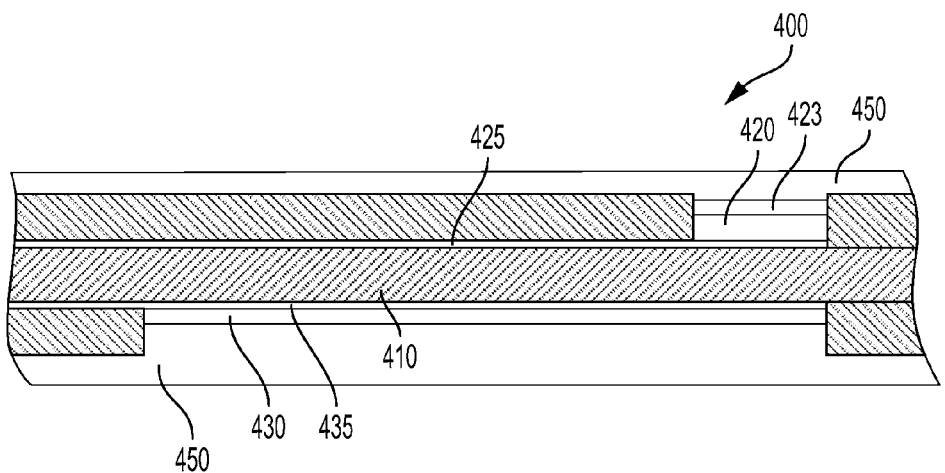
FIG. 4C is a cross-sectional view of the example electrochemical sensor of FIGS. 4A and 4B.

FIGS. 4A-C show an example sensor 400 that includes an elongate substrate 410 on which first 420 and second 430 electrodes and first 425 and second 435 conductive traces are disposed. FIGS. 4A and 4B show opposite sides of the sensor 400, and FIG. 4C shows a cross-section view through the end of the sensor 400. The first 420 and second 430 electrodes and first 425 and second 435 conductive traces are located on opposite sides of the elongate substrate 410. The sensor 400 is configured to penetrate skin such that the first and second electrodes 420, 430, are in contact with fluid (e.g., interstitial fluid) within the skin. Further, the first electrode 420 is selectively sensitive to an analyte such that the first and second electrodes 420, 430 can be operated to detect the analyte electrochemically (e.g., potentiometrically, amperometrically). The sensor 400 could be part of sensors and/or sensor probes as described elsewhere herein.

The elongate substrate 410 could include a flexible material, a rigid material, or a combination of flexible and rigid materials. For example, the elongate substrate 410 could include polyimide. The elongate substrate 410 could be configured to penetrate and/or pierce skin (e.g., by being sufficiently rigid and/or sharpened). Additionally or alternatively, the elongate substrate 410 could be configured to penetrate skin in combination with some other elements (e.g., in combination with a half-needle to which the elongate substrate 410 is coupled) and/or to penetrate an existing puncture, cut, or other incision into skin (provided, e.g., by a needle, lancet, scalpel, or other device). The elongate substrate 410 could be composed of a material on which conductive traces can be formed (e.g., by sputtering, CVD, photoresistive processes, or some other methods) and/or could be coated with a material such that conductive traces can be formed on the elongate substrate 410.

The first and second conductive traces 425, 435 are in electrical contact with the first and second electrodes 420, 430. The first and second conductive traces 425, 435 could provide an electrical connection between the first and second electrodes 420, 430 and electronics configured to operate the first and second electrodes 420, 430 to electrochemically detect an analyte (e.g., 130, 230, 352). Additionally or alternatively, the first and second conductive traces 425, 435 could provide an electrical connection between the first and second electrodes 420, 430 and electrical pads or other means for electrical connection disposed elsewhere on the elongate substrate 410. The first and second conductive traces 425, 435 could be composed of gold, platinum, palladium, titanium, copper, aluminum, silver, other metals, or combinations of these elements. The first and second conductive traces 425, 435 could have a specified thickness (e.g., between approximately 5 microns and approximately 10 microns) such that the first and second conductive traces 425, 435 provide a sufficiently high conductivity to allow operation of the first and second electrodes 420, 430 to electrochemically detect the analyte. Further, the first and second conductive traces 425, 435 could be covered by a passivation layer (e.g., a layer of parylene) to prevent conduction between the first and second conductive traces 425, 435 and fluids or other media surrounding the first and second conductive traces 425, 435.

The first and second electrodes 420, 430 could be composed of similar or different materials, and could include a variety of surface treatments and/or materials disposed thereon, according to an application. In some examples, the first electrode 420 could be a working electrode (i.e., an electrode that is selectively sensitive to the analyte) and the second electrode 430 could be a reference electrode (i.e., an electrode having a relatively stable electrode potential relative to the potential of a fluid with which the reference is in contact). The electrodes 420, 430 could be composed of a variety of materials and formed by a variety of methods. For example, the electrodes could be composed of metal that could be disposed at least partially on respective conductive traces 425, 435 by sputtering, CVD, electroplating, or some other method such that the first and second electrodes 420, 430 were disposed on the elongate substrate 410 in electrical contact with respective first 425 and second 435 conductive traces. In a particular example, the first 420 and/or second 430 electrode could be formed by electroplating metal on the first 425 and/or second 435 conductive trace (i.e., by submerging part of the first 425 and/or second 435 conductive traces in a bath containing a metal salt and/or other metal-containing compound and applying a current through the first 425 and/or second 435 conductive traces to cause deposition of the metal on the submerged portions of the first 425 and/or second 435 conductive traces).

An electrode (e.g., 430) configured to act as a reference electrode could be configured to provide a relatively stable voltage relative to a fluid with which it is in contact. Such configuration could include the composition of the reference electrode (e.g., the metal or other materials used to form the electrode), the structure of the reference electrode (e.g., the shape of the electrode, a micro-scale texture of the electrode, the configuration of multiple layers of material of the electrode), or other properties of a reference electrode. Further, such configuration could be related to properties of the fluid with which the electrode will be in contact and/or properties of the environment of the fluid and/or the electrode. For example, when the fluid is an aqueous fluid in regular contact with a sufficient source of oxygen (e.g., the fluid is a tear fluid or an eye), the reference electrode could include a surface layer composed of platinum (e.g., an approximately 100 nanometers to approximately 1 micron thick layer of platinum). In another example (e.g., where the fluid is an aqueous fluid that does not have access to a sufficient source of oxygen), the reference electrode could include a layer of silver chloride formed on a layer of silver (e.g., with a combined thickness of the silver and silver chloride layers being between approximately 2 microns and approximately 20 microns). Such a silver/silver chloride electrode could be formed by depositing a layer of silver and subsequently forming a silver chloride layer atop the silver layer by anodically oxidizing the silver layer. Such anodic oxidization could include submerging the deposited silver layer in an acidic solution containing a source of chloride ions (e.g., a 1M solution of hydrochloric acid) and passing a current through the silver layer to cause the chloride in the solution to form silver chloride on the silver layer.

An electrode (e.g., 420) configured to act as a working electrode could be made selectively sensitive to the analyte by immobilizing a substance (e.g., a reagent, a protein, an enzyme) that selectively interacts with the analyte on or near the working electrode of the sensor. Such an analyte-selective substance can be immobilized on the surface of the working electrode by crosslinking the substance into a crosslinked layer on the surface of the electrode. This could include using an aldehyde, dialdehyde (e.g., glutaraldehyde), or other crosslinking agents to form the crosslinked layer of the substance on the electrode surface. Additionally or alternatively, such an analyte-selective substance can be localized within an analyte-permeable polymer layer (e.g., 423) that is disposed on the working electrode.

The analyte-selective substance can be disposed within a polymer layer 423 formed on the surface of the working electrode. Such a polymer layer 423 can be permeable to the analyte and contain a reagent that selectively reacts with the analyte to create a reaction product that can be sensed directly by an electrode and/or by some other element (e.g., a fluorophore or other substance that selectively interacts with the reaction product). In some examples, the polymer layer 423 is a hydrogel that includes 2-hydroxyethyl methacrylate units. Such a hydrogel could contain additional polymer units or other chemicals to adjust a permeability of the hydrogel to the analyte, to bind the analyte-selective substance within the hydrogel, to increase a degree of crosslinking of the hydrogel, or to specify one or more other properties of the hydrogel. For example, such a hydrogel could additionally include di(ethylene glycol) dimethacrylate units. The polymer layer 423 could be formed on the working electrode 420 by forming a solution containing monomer units (e.g., units of 2-hydroxyethyl methacrylate), crosslinker units (e.g., units of di(ethylene glycol) dimethacrylate), copolymer units, the analyte-selective substance, and/or a polymerization initiator (e.g., the photoinitiator 2,2-dimethoxy-2-phenylacetophenone), depositing the formed solution on the working electrode 420, and polymerizing the solution into the polymer layer 423 containing the analyte-selective substance. In some examples, a permeability, thickness, or other properties of such an analyte-permeable layer could be specified to control a rate of diffusion of the analyte from interstitial fluid to the surface of the working electrode (e.g., the polymer layer 423 could have a thickness between approximately 5 microns and approximately 20 microns).

In some examples, the analyte-selective substance could be configured to selectively cause a chemical reaction of the analyte, and one or more reaction products of the reaction could be detected (e.g., potentiometrically, amperometrically) by the working electrode. For example, the analyte-selective substance could include an agent that selectively oxidizes and/or reduces the analyte (e.g., the analyte-selective substance could be an oxidoreductase enzyme or protein). For example, the analyte could be glucose, pyruvate, or urea and the analyte-selectively substance could be glucose oxidase, pyruvate oxidase, or urease, respectively. Such a reaction could produce reaction products including oxides (e.g., hydrogen peroxide) and the working electrode 420 could be configured to detect those oxides. For example, the reaction products could include hydrogen peroxide and the working electrode 420 could include a layer platinum (e.g., a layer of platinum having a thickness between approximately 1 micron and approximately 5 microns).

The sensor 400 additionally includes a protective layer 450 disposed over elements of the sensor 400 including the first 420 and second 430 electrodes. This protective layer 450 could be composed of a polymer, gel, or other material that is permeable to the analyte In some examples, a permeability, thickness, or other properties of such the protective layer 450 could be specified to control a rate of diffusion of the analyte from interstitial fluid to the working electrode 420 and/or to the polymer layer 423 containing the analyte-selective substance. In some examples, the protective layer 450 could be a hydrogel, e.g., a hydrogel that includes units of 2-hydroxethyl methacrylate and/or units of di(ethylene glycol) dimethacrylate. Additionally or alternatively, the protective layer 450 could include one or more polymers, including polydimethylsiloxane, polyvinylchloride, polyethylene terephthalate, polymethyl methacrylate, silicone hydrogels, or combinations of these or other polymers. Note that, while the illustrated protective layer 450 covers substantially the entire sensor 400, a protective layer could be formed to cover less of a sensor 400, e.g., to only cover the reference electrode 430 and/or working electrode 420.

The protective layer 450 could be formed by a variety of processes, including CVD, application of a monomer solution followed by polymerization, precipitation of elements of the protective layer 450 from a solution into which the sensor 400 has been dipped, or some other methods. For example, the sensor 400 (and/or some terminal aspect thereof, e.g., a specified length of the distal end of sensor 400) could be dipped in a solution containing a monomer, co-monomer, crosslinker, and/or other chemicals (e.g., units of 2-hydroxethyl methacrylate and/or units of di(ethylene glycol) dimethacrylate), and the solution applied to the sensor 400 could then be polymerized to form the protective layer 450.

The areas of electrodes of a sensor (e.g., 400) could be specified according to an application. For example, the area of a working electrode of an amperometric sensor could be specified such that the sensor has a specified current gain (i.e., such that a relationship between a measured current through the working electrode and the concentration of an analyte in fluid to which the working electrode is exposed has some specified value and/or has some value within some specified range of values). For example, a working electrode of an amperometric sensor could have an area between approximately 0.05 square millimeters and approximately 0.5 square millimeters. Further, a reference electrode of an amperometric sensor could have an area sufficiently large that, when a return current passes through the reference electrode, the relative voltage between the reference electrode and the fluid to which the reference electrode is exposed is within an acceptable range of the zero-current relative voltage of the reference electrode. For example, a reference electrode of an amperometric sensor could have an area between approximately 0.5 square millimeters and approximately 3.0 square millimeters.

Figure 5:
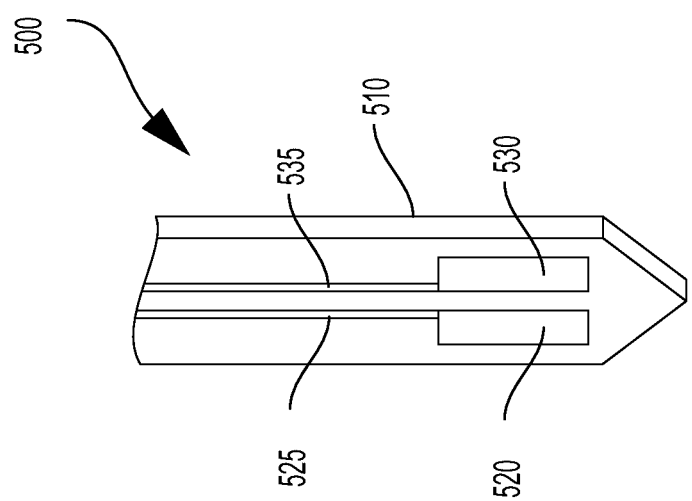
FIG. 5 is an aspect view of an example electrochemical sensor.

Note that the arrangements, shapes, presence, sizes, and other properties of elements of an electrochemical sensor as illustrated in FIGS. 4A-4C are intended as non-limiting examples. For example, first and second electrodes of an electrochemical sensor could be disposed on the same side of substrate. FIG. 5 shows an example sensor 500 that includes an elongate substrate 510 on which first 520 and second 530 electrodes and first 525 and second 535 conductive traces are disposed. The first 520 and second 530 electrodes and first 525 and second 535 conductive traces are located on the same side of the elongate substrate 510. The first and second electrodes 520, 530 could be located on the same side of the elongate substrate 520 to reduce the number of steps required to fabricate the sensor 500. Additionally or alternatively, the first and second electrodes 520, 530 could be located on the same side of the elongate substrate 520 to reduce a distance between the first and second electrodes 520, 530, e.g., to increase a sensitivity of the sensor 500 to an analyte.

Figure 6:
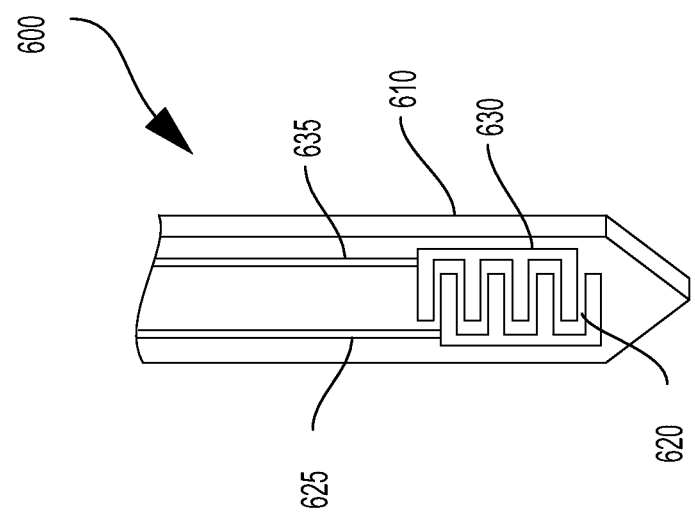
FIG. 6 is an aspect view of an example electrochemical sensor.

Further configurations of electrodes of an electrochemical sensor are anticipated. For example, aspects of first and second electrodes could be interdigitated to increase a sensitivity of an amperometric electrochemical sensor (e.g., by decreasing a distance between first and second electrodes and/or increasing an amount of area that is immediately between first and second electrodes). FIG. 6 shows an example sensor 600 that includes an elongate substrate 610 on which interdigitated first 620 and second 630 electrodes and first 625 and second 635 conductive traces are disposed.

In some examples, the sensor of a sensing platform can include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of a substance disposed at the end of the sensor probe could be related to the presence, concentration, or some other property of the analyte. The sensor and/or a sensor platform including the sensor could include a light emitter and/or a light detector configured to illuminate and/or to receive light emitted from the analyte-sensitive substance, respectively, in order to determine the optical property of the substance that is related to the analyte.

Figure 7:
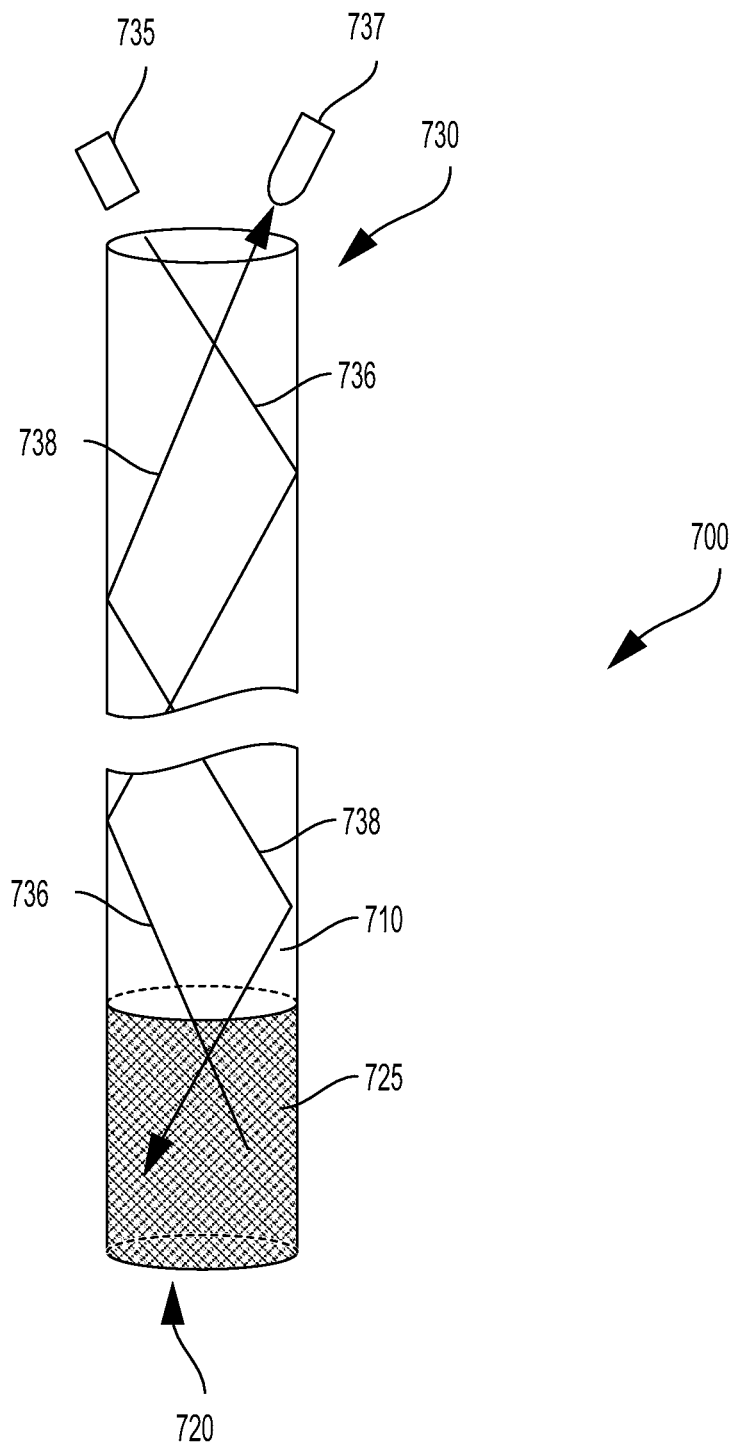
FIG. 7 is an aspect view of an example optical sensor.

FIG. 7 shows a sensor probe 700 that includes an optical fiber 710. The optical fiber has a distal end 720 on which an analyte-selective substance 725 is disposed. The distal end 720 is configured to contact a fluid (e.g., interstitial fluid) and the analyte-selective substance 725 is configured to have an optical property (e.g., a fluorescence, a fluorescence lifetime, a color, an absorption spectrum) that is related to the presence, concentration, or other property of the analyte in the fluid to which the analyte-selective substance 725 is exposed. A light emitter 735 (e.g., an LED, a laser, etc.) and a light detector 737 (e.g., a photodiode, a phototransistor, a photoresistor, etc.) are disposed at a proximal end 730 of the optical fiber 710. The optical fiber 710 is configured (e.g., is composed of a material that is optically transparent across one or more ranges of wavelengths of light) such that the light emitter 735 can emit illumination 738 to illuminate the analyte-selective substance 725 via the optical fiber 710. Further, the light detector 737 can detect responsively emitted light 738 that is emitted from the analyte-selective substance 725 via the optical fiber 710.

Note that the sensor 700 could include elements additional to those shown. In some examples, the analyte-selective substance 725 could be disposed in a layer of polymer, gel, or other analyte-permeable material 725 disposed at the distal end 720 of the optical fiber 710. Additionally or alternatively, a protective layer could be disposed over the analyte-permeable material 725. In some examples, the optical fiber 710 could be disposed on (e.g., adhered to, formed on) a flexible substrate that is, in turn, continuous with a flexible substrate that is configured to be mounted to a skin surface and on which electronics (including, e.g., the light emitter 735 and light detector 737) could be disposed. Further, one or both of the light emitter 735 and light detector 737 could be disposed proximate the analyte-selective substance 725 such that the light emitter 735 and/or light detector 737 could illuminate and/or receive emitted light from, respectively, the analyte-selective substance 725 directly rather than through an optical fiber (e.g., 710). In such examples, the light emitter 735, light detector 737, and/or analyte-selective substance 725 could be disposed on the distal end of a sensor probe as described in connection with other embodiments described herein (e.g., embodiments described in relation to FIGS. 1A, 1B, and 2A-2D).

Moreover, it is particularly noted that while analyte sensors and body-mountable sensor platforms including such sensors are described herein by way of example as a body-mountable, skin-penetrating and/or skin-surface-mounted devices, it is noted that the disclosed sensors, electrode arrangements, and sensing platforms can be applied in other contexts as well. For example, sensors and sensing platforms disclosed herein may be included in body-mountable and/or implantable sensors and/or sensing platforms used to measure an analyte in a fluid of an animal. In another example, sensors and/or sensing platforms disclosed herein may be included in devices to measure an analyte in an environmental fluid, such as a fluid in a river, lake, marsh, reservoir, water supply, sanitary sewer system, or storm sewer system. In another example, sensors and/or sensing platforms disclosed herein may be included in devices to measure an analyte in a fluid which is part of a process, such as a waste treatment process, pharmaceutical synthesis process, food preparation process, fermentation process, or medical treatment process

V. Example Methods

Figure 8:
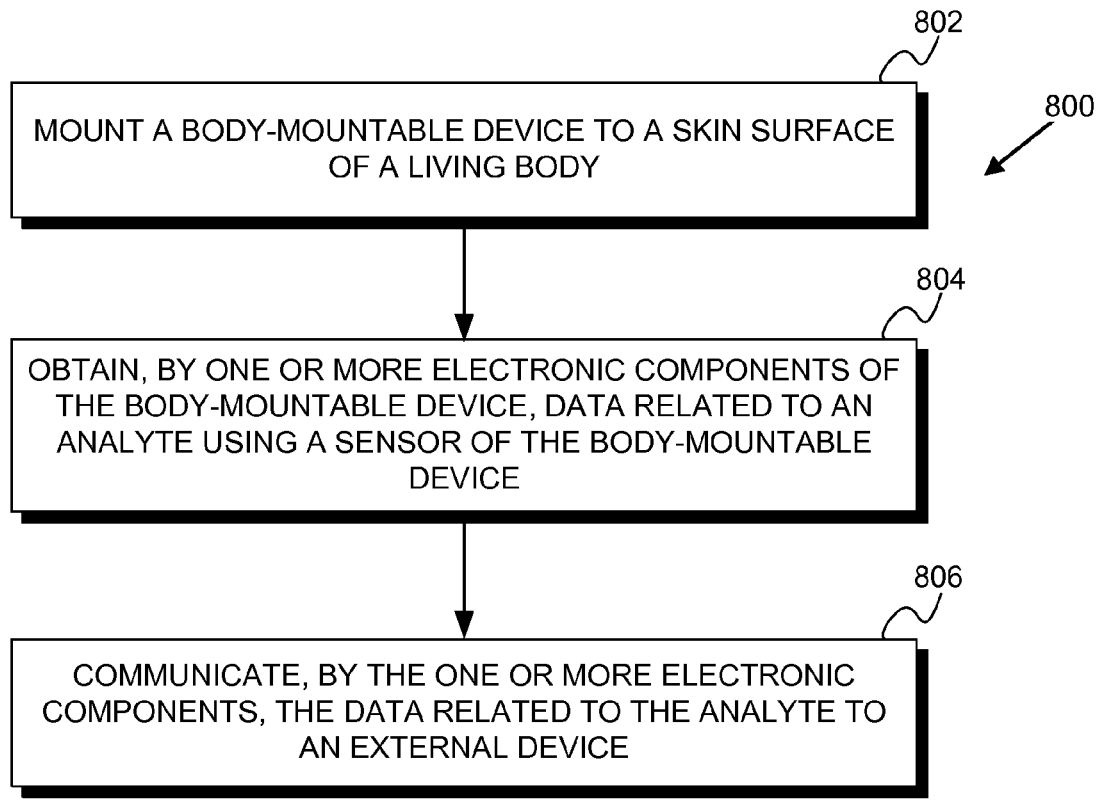
FIG. 8 is a flowchart of an example process for operating a body-mountable device.

FIG. 8 is a flowchart of a method 800 for operating a body-mountable device to measure an analyte in a fluid of a body. The body-mountable device includes (i) a flexible substrate configured to be mounted to a skin surface of a living body, (ii) a sensor probe that has a proximal end attached to the flexible substrate and that is configured to extend into the skin of the living body to a depth sufficient to contact interstitial fluid, (iii) a sensor that is disposed at the distal end of the sensor probe and that is configured to detect an analyte in the interstitial fluid, and (iv) one or more electronic components disposed on the substrate.

The method 800 includes mounting the body-mountable device to the skin surface of the living body (802). Mounting the body-mountable device to the skin surface (802) could include using an adhesive layer of the body-mountable device to mount the flexible substrate to the skin surface. Additionally or alternatively, a liquid adhesive, tape, strap, dry adhesive, or other means could be used to mount the flexible substrate to the skin surface. Further, mounting the body-mountable device to the skin surface (802) could include installing the sensor probe in the skin such that the sensor probe penetrates the skin and further such that the sensor disposed on the sensor probe is placed in contact with a fluid (e.g., interstitial fluid) within the skin. This could include placing the sensor probe in a puncture, cut, or other incision that has already been formed in the skin (e.g., by a needle, a lancet, a scalpel, or by some other means). Alternatively, the sensor probe could be configured to penetrate and/or pierce the skin (e.g., by being sharpened and/or having a sufficiently high rigidity).

In some examples, mounting the body-mountable device to the skin surface (802) could include using some sort of insertion device or insertion aid to emplace the sensor probe in the skin. In some examples, this could include coupling the sensor probe to a needle (e.g., placing the sensor probe in the channel of a half-needle) and piercing skin using the needle such that the needle and the coupled sensor probe penetrate the skin. That is, the needle is sufficiently rigid and/or has an end that is sufficiently sharp that force can be applied to the needle such that the needle pierces the skin. The needle (and any apparatus of which it is a part) can then be moved away from the skin, retracting the needle while the sensor probe remains inserted in (i.e., penetrating) the skin and the flexible substrate remains mounted on the skin surface. Use of the needle to pierce skin (e.g., by applying sufficient force to the needle) could be performed manually (e.g., by manual manipulation of an insertion device that includes the needle) or automatically (e.g., by operation of (e.g., a spring-loaded mechanism, a servomechanism including one or more solenoids, motors, or other electromechanical actuators) by a system configured to drive the needle (and sensor probe coupled thereto) into skin (e.g., to a specified depth within the skin, at a sufficiently high speed to minimize user discomfort).

The method 800 additionally includes obtaining, by one or more of the electronic components of the body-mountable device, data related to the analyte using the sensor (804). In some examples, the sensor could be a potentiometric electrochemical sensor, and obtaining analyte data (804) could include measuring a voltage between two or more electrodes. In some examples, the sensor could be an amperometric electrochemical sensor, and obtaining analyte data (804) could include applying a specified voltage between two or more electrodes and measuring a current through one of the two or more electrodes. In some examples, the sensor could be an optical sensor, and obtaining analyte data (804) could include illuminating and/or detecting light emitted from a substance that is in contact with a fluid and that has one or more optical properties related to the analyte in the fluid. Obtaining analyte data (804) could include determining a concentration of the analyte in a fluid, determining that the analyte is present in the fluid (e.g., that the concentration of the analyte in the fluid is above some threshold), determining that the concentration of the analyte is within some specified range of concentrations, determining a state of the analyte (e.g., determining a distribution of isoforms and/or conformational states of the analyte in the fluid), or determining some other information about the analyte. Obtaining analyte data (804) could include determining a concentration or other information about the analyte at a plurality of different points in time (e.g., at a specified rate). Obtaining analyte data (804) could be performed in response to a request for such data (e.g., by an external system in communication with the body-mountable device).

The method 800 additionally includes communicating, by one or more of the electronic components of the body-mountable device, the data related to the analyte to an external device (806). Communicating analyte data (806) could be performed periodically, in response to a request for such data (e.g., from an external system in communication with the body-mountable device), in response to the determination that an event has occurred and/or a specified condition is satisfied (e.g., in response to a determination by the body-mountable device of a particular health state of a body to which the device is mounted). Communicating analyte data (806) could be performed securely, e.g., by encrypting information that is transmitted. Communicating analyte data (806) could include transmitting additional data, e.g., information about the status of the device (e.g., battery charge status, memory free space status), other information gathered by the device (e.g., temperature data obtained using a temperature sensor of the device), user inputs to the device (e.g., taps, swipes, or other inputs to buttons, capacitive sensors, or other elements of the device to control the device, indicate user states or information or according to some other application), or some other information.

The method 800 could include additional steps. For example, the method 800 could include using a memory of the device to store information relating to the analyte (e.g., detected analyte concentration values). The method 800 could include determining a health state, a course of treatment, a dose and/or timing of administration of a drug, or some other information based on detected analyte data. The method 800 could include indicating detected analyte data, determined dosing and/or timing of administration of a drug, or some other information generated by and/or available to the device using a user interface of the device (e.g., LEDs, displays, vibrators) and/or via a user interface of an external device in communication with the device. Additional and/or alternative steps, or alternative embodiments of the listed steps, are anticipated.

Figure 9:
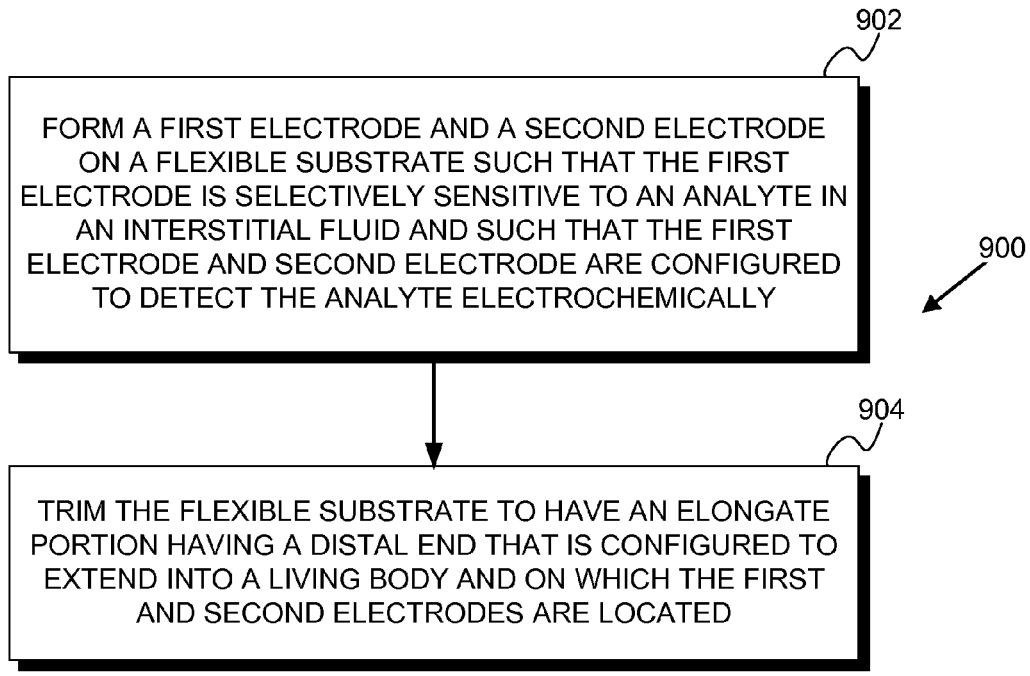
FIG. 9 is a flowchart of an example process for fabricating a sensor.

FIG. 9 is a flowchart of a method 900 for fabricating a sensor (e.g., a sensor that is a part of a body-mountable sensing platform as described elsewhere herein). The method includes forming a first electrode and a second electrode on a flexible substrate such that the first electrode is selectively sensitive to an analyte in an interstitial fluid and such that the first and second electrodes are configured to detect the analyte electrochemically (902). Forming first and second electrodes (902) could include forming metal contacts, traces, and/or interconnects directly on the surface of the flexible substrate (e.g., by sputtering, CVD, or some other deposition process) and/or on a coating or layer formed on one or more surfaces of the flexible substrate. Further, the method 900 could include depositing conductive traces on the flexible substrate (e.g., traces configured to electrically connect between the electrodes and access pads formed elsewhere on the substrate and/or between the electrodes and electronics disposed on the flexible substrate); in such examples, forming first and second electrodes (902) could include forming the electrodes at least partially on the disposed conductive traces (e.g., to provide electrical contact between the electrodes and the conductive traces). Further, in such examples forming first and second electrodes (902) could include electroplating the conductive traces to from the electrodes.

Forming first and second electrodes (902) could include additional steps. For example, one or both of the electrodes could be a silver/silver chloride electrode that could be formed by depositing a layer of silver on the flexible substrate and subsequently forming a layer of silver chloride on the silver layer. The layer of silver chloride on the silver layer could be formed through a process of anodic oxidization that includes submerging the deposited silver layer in an acidic solution containing a source of chloride ions (e.g., a 1M solution of hydrochloric acid) and passing a current through the silver layer to cause the chloride in the solution to form silver chloride on the silver layer. Forming first and second electrodes (902) could include making the first electrode sensitive to the analyte by disposing an analyte-selective substance on the first electrode. In some examples, this could include crosslinking the analyte-selective substance into a crosslinked layer on a surface of the electrode (e.g., by using an aldehyde, dialdehyde, glutaraldehyde, or some other crosslinking agent). In some examples, this could include forming an analyte-permeable polymer layer that contains the analyte-selective substance. Such a polymer layer could be a hydrogel (e.g., a hydrogel containing 2-hydroxethyl methacrylate units and/or some other polymer, copolymer, crosslinker, or other units).

The method 900 additionally includes trimming the substrate to have an elongate portion having a distal end that is configured to extend into a living body and on which the first and second electrodes are located (904). This could include stamping, cutting, laser cutting, etching, or some other process such that the flexible substrate is formed to have a specified shape, wherein the specified shape includes an elongate portion that can penetrate skin of a living body and that, when it penetrates skin, places the electrodes disposed on the flexible substrate in contact with fluid (e.g., interstitial fluid) within the skin. Trimming the substrate (904) could include forming the substrate to have a specified shape according to additional applications, e.g., such that aspects of the trimmed substrate that are not the elongate portion can be mounted to a skin surface of the living body.

The method 900 could include additional steps. The method 900 could include forming a protective layer (e.g., a layer of a protective polymer, a hydrogel, or some other protective material) over all or part of the flexible substrate and/or elements disposed thereon. For example, a protective hydrogel layer could be formed on the elongate portion of the flexible substrate (e.g., covering the electrodes). Such a protective layer could be formed by dipping the elongate portion in a solution comprising monomer units (e.g., comprising 2-hydroxyethyl methacrylate units and/or some other polymer, copolymer, crosslinker, or other units) and subsequently polymerizing the solution disposed on the flexible substrate by dipping. The method 900 could include forming antennas, interconnects, or other elements on the flexible substrate (e.g., by patterning metal or other conductive material on the flexible substrate). The method 900 could include disposing components on the flexible substrate. Components such as electronic chips may be disposed on the substrate and connected to the other components by methods familiar to one skilled in the art (e.g., pick-and-place machines, flip-chip mounting). The method 900 could include a calibration step, wherein the electrodes are exposed to test fluids having a range of known analyte concentrations. Analyte concentrations or other information about the analyte measured using the electrodes when exposed to respective fluids having known concentrations of the analyte could be used to calibrate the electrochemical sensor. Additional and/or alternative steps, or alternative embodiments of the listed steps, are anticipated.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
    a flexible substrate having a first side and a second side opposite the first side, wherein the flexible substrate is mountable to a skin surface, and wherein the flexible substrate is shaped to have an elongate extension having a distal end configured to extend beneath the skin surface to contact interstitial fluid;
    an adhesive layer disposed on the first side of the flexible substrate, wherein the adhesive layer is configured to adhere the flexible substrate to the skin surface;
    a sensor, wherein the sensor is disposed at the distal end of the elongate extension, and wherein the sensor is configured to detect an analyte in the interstitial fluid;
    one or more electronic components disposed on the flexible substrate, wherein the one or more electronic components are configured to (i) use the sensor to obtain data related to the analyte and (ii) communicate the data related to the analyte to an external device, wherein at least one of the one or more electronic components is disposed on the first side of the flexible substrate; and
    a battery, wherein the battery is disposed on the flexible substrate.

2. The body-mountable device of claim 1, wherein the flexible substrate comprises polyimide.

3. The body-mountable device of claim 1, wherein the flexible substrate and the one or more electronic components disposed thereon have a combined thickness of less than 0.5 millimeters.

4. The body-mountable device of claim 1, wherein the flexible substrate has a diameter of less than 11 millimeters.

5. The body-mountable device of claim 1, wherein the elongate extension of the flexible substrate has a length greater than 2 millimeters.

6. The body-mountable device of claim 1, further comprising an antenna disposed on the flexible substrate, wherein the electronic components are configured to communicate the data related to the analyte to the external device using the antenna.

7. The body-mountable device of claim 1, wherein the one or more electronic components include a memory configured to store the data related to the analyte.

8. The body-mountable device of claim 1, wherein the battery comprises a flexible lithium ion battery.

9. The body-mountable device of claim 1, wherein the sensor comprises at least two electrodes and is configured to detect the analyte electrochemically.

10. The body-mountable device of claim 1, further comprising an optical fiber disposed on the elongate extension of the flexible substrate, wherein the optical fiber extends from a proximal end of the elongate extension to the distal second end of the elongate extension, wherein the sensor comprises an analyte-sensitive chemical, wherein the analyte-sensitive chemical has an optical property that is related to the analyte, wherein the one or more electronic components include a light emitter, a light detector, and a controller configured to (i) operate the light emitter to illuminate, via the optical fiber, the analyte-sensitive chemical and (ii) operate the light detector to detect, via the optical fiber, a property of light emitted from the analyte-sensitive chemical in response to the illumination, wherein the detected property of the emitted light is related to the analyte.

11. The body-mountable device of claim 1, further comprising a conductive trace patterned on a surface of the flexible substrate, wherein the battery is connected to the flexible substrate via the conductive trace.

12. The body-mountable device of claim 1, wherein the adhesive layer is disposed on the first side of the flexible substrate such that the adhesive layer covers the at least one of the one or more electronic components that is disposed on the first side of the flexible substrate.

13. The body-mountable device of claim 1, wherein at least one of the one or more electronic components is disposed on the second side of the flexible substrate.

14. A method comprising:
    mounting a body-mountable device to a skin surface, wherein the body-mountable device comprises:
        a flexible substrate having a first side and a second side opposite the first side, wherein the flexible substrate is mountable to a skin surface, and wherein the flexible substrate is shaped to have an elongate extension having a distal end configured to extend beneath the skin surface to contact interstitial fluid;
        an adhesive layer disposed on the first side of the flexible substrate, wherein the adhesive layer is configured to adhere the flexible substrate to the skin surface;
        a sensor, wherein the sensor is disposed on the distal end of the elongate extension, and wherein the sensor is configured to detect an analyte in the interstitial fluid;
        one or more electronic components disposed on the flexible substrate, wherein at least one of the one or more electronic components disposed on the flexible substrate is disposed on the first side of the flexible substrate; and
        a battery, wherein the battery is disposed on the flexible substrate;
    operating the body-mountable device to obtain, by the one more electronic components, data related to the analyte using the sensor; and
    operating the body-mountable device to communicate, by the one or more electronic components, the data related to the analyte to an external device.

15. The method of claim 14, wherein the body-mountable device further comprises an antenna disposed on the flexible substrate, and wherein communicating, by the one or more electronic components, the data related to the analyte to an external device comprises:
    communicating the data related to the analyte via the antenna.

16. The method of claim 14, wherein the one or more electronic components include a memory, and further comprising:
    operating the body-mountable device to store the data related to the analyte in the memory.

17. The method of claim 14, further comprising:
coupling the elongate extension of the flexible substrate to a needle; and
inserting the needle with the elongate extension of the flexible substrate coupled thereto into the skin surface such that the sensor is in a position to contact interstitial fluid.

18. The method of claim 17, further comprising:
retracting the needle from the skin surface such that the sensor remains in the position to contact interstitial fluid.

19. The method of claim 14, wherein the body-mountable device further comprises a conductive trace patterned on a surface of the flexible substrate, wherein the battery is connected to the flexible substrate via the conductive trace.

20. The method of claim 14, wherein at least one of the one or more electronic components is disposed on the second side of the flexible substrate.

* * * * *